United States Patent
Ream et al.

(10) Patent No.: US 6,322,806 B1
(45) Date of Patent: Nov. 27, 2001

(54) OVER-COATED CHEWING GUM FORMULATIONS INCLUDING TABLETED CENTER

(75) Inventors: Ronald L. Ream, Plano; Christine L. Corriveau, Orland Park; Gwendolyn Graff, DeKalb; Leonard Matulewicz, Oswego, all of IL (US)

(73) Assignee: Wm. Wrigley Jr. Company, Chicago, IL (US)

( * ) Notice: Subject to any disclaimer, the term of this patent is extended or adjusted under 35 U.S.C. 154(b) by 0 days.

(21) Appl. No.: 09/618,808

(22) Filed: Jul. 18, 2000

Related U.S. Application Data

(63) Continuation-in-part of application No. 09/510,878, filed on Feb. 23, 2000, which is a continuation-in-part of application No. PCT/US99/29742, filed on Dec. 14, 1999, and a continuation-in-part of application No. 09/286,818, filed on Apr. 6, 1999.

(51) Int. Cl.$^7$ .................. A61K 9/68; A61K 9/20
(52) U.S. Cl. ............... 424/440; 424/48; 424/464
(58) Field of Search ................ 424/400, 48, 439, 424/440, 464; 426/5

(56) References Cited

U.S. PATENT DOCUMENTS

| | | |
|---|---|---|
| 1,298,670 | 4/1919 | Cramer . |
| 1,629,461 | 5/1927 | Berg et al. . |
| 2,892,753 | 6/1959 | Schmidt et al. ............ 167/65 |
| 2,990,328 | 6/1961 | Lincoln ...................... 167/55 |

(List continued on next page.)

FOREIGN PATENT DOCUMENTS

| | | |
|---|---|---|
| 43 42 568 | 6/1984 | (DE) . |
| 0202819 A2 | 11/1986 | (EP) . |
| 1217109 A2 | 4/1987 | (EP) . |
| 0 221 850 | 5/1987 | (EP) . |

OTHER PUBLICATIONS

Akitoshi et al., Abstract "Acceleration of Transdermal Absorption of Pharmaceuticals by Essential Oils and Organic Solvents," Chem. Abst., 112:125228t, 1990.

Bradford, A Rapid and Sensitive Method for the Quantification of Microgram Quantities of Protein Utilizing the Principle of Protein–Dye Binding, Analytical Biochemistry, 72:248–254 (1976).

Nielsen et al., P–Glycoprotein as Multidrug Trnasporter: A Critical Review of Current Multidrug Resistant Cell Lines, Chimica et Biophysica Acta., 1139: 169–183 (1992).

(List continued on next page.)

Primary Examiner—Thurman K. Page
Assistant Examiner—S. Howard
(74) Attorney, Agent, or Firm—Bell, Boyd & Lloyd LLC

(57) ABSTRACT

Methods and products for delivering a medicament or agent to an individual are provided as well as methods for producing the product. The product includes a coating having a medicament or agent. The medicament or agent is present within the coating that surrounds a tableted gum center (the water soluble portion and a water insoluble base portion). By chewing the gum, the medicament or agent is released from the product. Continuing to chew the chewing gum creates a pressure within the buccal cavity forcing the agent or medicament directly into the systemic system of the individual through the oral mucosa contained in the buccal cavity. This greatly enhances the absorption of the drug into the systemic system as well as the bioavailability of the drug within the system.

36 Claims, 3 Drawing Sheets

U.S. PATENT DOCUMENTS

| | | | |
|---|---|---|---|
| 3,011,949 | 12/1961 | Bilotti | 167/82 |
| 3,029,189 | 4/1962 | Hardy, Jr. et al. | 167/65 |
| 3,047,461 | 7/1962 | Hardy, Jr. et al. | 167/65 |
| 3,075,884 | 1/1963 | Bilotti et al. | 167/82 |
| 3,196,172 | 7/1965 | Wright, Jr. et al. | 260/471 |
| 3,308,022 | 3/1967 | Cummings et al. | 167/65 |
| 3,498,964 | 3/1970 | Hayashi | 260/112 |
| 3,554,767 | 1/1971 | Daum . | |
| 3,590,057 | 6/1971 | Suzuki et al. | 260/404 |
| 3,845,217 | 10/1974 | Ferno et al. | 426/3 |
| 3,877,468 | 4/1975 | Lichtneckert et al. | 131/2 |
| 3,901,248 | 8/1975 | Lichtneckert et al. | 131/2 |
| 3,995,064 | 11/1976 | Ehrgott et al. . | |
| 4,154,814 | 5/1979 | Hand et al. | 424/48 |
| 4,238,475 | 12/1980 | Witzel et al. | 424/48 |
| 4,238,510 | 12/1980 | Cherukuri et al. . | |
| 4,283,408 | 8/1981 | Hirata et al. . | |
| 4,317,838 | 3/1982 | Cherukuri et al. . | |
| 4,386,063 | 5/1983 | Boden | 424/49 |
| 4,400,372 | 8/1983 | Muhler et al. | 424/48 |
| 4,446,135 | 5/1984 | Fountaine . | |
| 4,452,821 | 6/1984 | Gergely | 426/5 |
| 4,459,311 | 7/1984 | DeTora et al. . | |
| 4,474,749 | 10/1984 | Kruppa | 424/48 |
| 4,512,968 | 4/1985 | Komiyama et al. | 424/48 |
| 4,533,526 | 8/1985 | Piccolo et al. | 426/3 |
| 4,555,407 | 11/1985 | Kramer et al. . | |
| 4,563,345 | 1/1986 | Arrick | 424/48 |
| 4,639,368 | 1/1987 | Niazi et al. | 424/48 |
| 4,647,450 | 3/1987 | Peters et al. | 424/48 |
| 4,711,774 | 12/1987 | Denick, Jr. et al. | 424/48 |
| 4,716,033 | 12/1987 | Denick, Jr. | 424/48 |
| 4,737,366 | 4/1988 | Gergely et al. | 426/5 |
| 4,753,800 | 6/1988 | Mozda | 424/440 |
| 4,753,805 * | 6/1988 | Cherukuri et al. | 426/5 |
| 4,755,389 | 7/1988 | Jones et al. | 424/456 |
| 4,758,424 | 7/1988 | Denick, Jr. et al. | 424/48 |
| 4,822,597 | 4/1989 | Faust et al. | 424/48 |
| 4,822,816 | 4/1989 | Markham | 514/474 |
| 4,828,820 | 5/1989 | Glass et al. | 424/48 |
| 4,832,994 | 5/1989 | Fey | 424/48 |
| 4,835,162 | 5/1989 | Abood | 514/305 |
| 4,849,227 | 7/1989 | Cho | 424/498 |
| 4,853,212 | 8/1989 | Faust et al. | 424/48 |
| 4,867,989 | 9/1989 | Silva et al. | 426/5 |
| 4,882,152 | 11/1989 | Yang et al. . | |
| 4,894,234 | 1/1990 | Sharma et al. | 426/5 |
| 4,908,211 | 3/1990 | Paz | 424/440 |
| 4,908,212 | 3/1990 | Kwon et al. | 424/440 |
| 4,929,447 | 5/1990 | Yang | 424/440 |
| 4,929,508 | 5/1990 | Sharma et al. | 424/439 |
| 4,933,184 | 6/1990 | Tsuk | 424/449 |
| 4,935,242 | 6/1990 | Sharma et al. | 424/439 |
| 4,938,963 | 7/1990 | Parnell | 424/440 |
| 4,944,949 | 7/1990 | Story et al. | 424/451 |
| 4,963,369 | 10/1990 | Song et al. | 426/5 |
| 4,968,511 | 11/1990 | D'Amelia et al. . | |
| 4,968,716 | 11/1990 | Markham | 514/474 |
| 4,971,079 | 11/1990 | Talapin et al. | 131/359 |
| 4,971,787 | 11/1990 | Cherukuri et al. | 414/48 |
| 4,975,270 | 12/1990 | Kehoe | 424/48 |
| 4,978,537 | 12/1990 | Song | 426/5 |
| 4,997,659 | 3/1991 | Yatka et al. . | |
| 5,013,716 | 5/1991 | Cherukuri et al. | 514/23 |
| 5,015,464 | 5/1991 | Strobridge | 424/48 |
| 5,045,325 | 9/1991 | Lesko et al. . | |
| 5,070,085 | 12/1991 | Markham | 514/161 |
| 5,124,156 | 6/1992 | Shibata et al. | 424/440 |
| 5,126,151 | 6/1992 | Bodor et al. | 426/99 |
| 5,139,787 | 8/1992 | Broderick et al. | 424/486 |
| 5,154,927 | 10/1992 | Song et al. | 424/440 |
| 5,156,842 | 10/1992 | Mulligan | 424/195.1 |
| 5,179,122 | 1/1993 | Greene et al. | 514/458 |
| 5,182,099 | 1/1993 | Jonsson et al. | 424/49 |
| 5,229,137 | 7/1993 | Wolfe . | |
| 5,244,670 | 9/1993 | Upson et al. . | |
| 5,284,657 | 2/1994 | Lu et al. | 424/435 |
| 5,286,500 | 2/1994 | Synosky et al. . | |
| 5,294,449 | 3/1994 | Greenberg | 426/3 |
| 5,340,566 | 8/1994 | Curtis et al. | 424/49 |
| 5,378,131 | 1/1995 | Greenberg | 424/440 |
| 5,380,530 | 1/1995 | Hill | 424/440 |
| 5,380,535 | 1/1995 | Geyer et al. | 424/484 |
| 5,397,580 | 3/1995 | Song et al. . | |
| 5,410,028 | 4/1995 | Asami et al. | 536/2 |
| 5,419,919 | 5/1995 | Song et al. . | |
| 5,433,960 * | 7/1995 | Meyers | 426/5 |
| 5,445,834 | 8/1995 | Burger et al. | 426/3 |
| 5,455,286 | 10/1995 | Amidon et al. | 523/122 |
| 5,456,677 | 10/1995 | Spector | 604/290 |
| 5,487,902 | 1/1996 | Andersen et al. | 426/3 |
| 5,488,962 | 2/1996 | Perfetti | 131/270 |
| 5,494,685 | 2/1996 | Tyrpin et al. | 426/5 |
| 5,496,541 | 3/1996 | Cutler | 424/50 |
| 5,512,306 | 4/1996 | Carlsson et al. | 426/3 |
| 5,523,097 | 6/1996 | Song et al. . | |
| 5,534,272 | 7/1996 | Bernstein | 426/3 |
| 5,543,160 | 8/1996 | Song et al. . | |
| 5,554,380 | 9/1996 | Cuca et al. | 424/441 |
| 5,569,477 | 10/1996 | Nesbitt . | |
| 5,571,528 | 11/1996 | Lee et al. | 424/440 |
| 5,571,543 | 11/1996 | Song et al. . | |
| 5,576,344 | 11/1996 | Sandler et al. . | |
| 5,580,590 | 12/1996 | Hartman | 426/3 |
| 5,582,855 | 12/1996 | Cherukuri et al. | 426/5 |
| 5,585,110 | 12/1996 | Kalili et al. | 424/440 |
| 5,593,685 | 1/1997 | Bye et al. | 424/439 |
| 5,605,698 | 2/1997 | Ueno | 424/440 |
| 5,607,697 | 3/1997 | Alkire et al. | 424/495 |
| 5,618,517 | 4/1997 | Miskewitz | 424/48 |
| 5,628,986 | 5/1997 | Sanker et al. | 424/49 |
| 5,629,013 | 5/1997 | Davis . | |
| 5,629,026 | 5/1997 | Davis . | |
| 5,629,035 | 5/1997 | Miskewitz | 426/5 |
| 5,645,853 | 7/1997 | Winston et al. | 424/440 |
| 5,656,652 | 8/1997 | Davis . | |
| 5,665,386 | 9/1997 | Benet et al. | 424/451 |
| 5,667,802 | 9/1997 | Grimberg | 424/464 |
| 5,693,334 | 12/1997 | Miskewitz | 424/440 |
| 5,698,215 | 12/1997 | Kalili et al. | 424/440 |
| 5,702,687 | 12/1997 | Miskewitz | 424/52 |
| 5,711,961 | 1/1998 | Reiner et al. | 424/441 |
| 5,716,928 | 2/1998 | Benet et al. | 514/11 |
| 5,736,175 | 4/1998 | Cea et al. | 426/6 |
| 5,744,164 | 4/1998 | Chauffard et al. | 424/496 |
| 5,753,255 | 5/1998 | Chavkin et al. | 424/441 |
| 5,756,074 | 5/1998 | Ascione et al. | 424/52 |
| 5,800,847 | 9/1998 | Song et al. . | |
| 5,824,291 | 10/1998 | Howard | 424/48 |
| 5,834,002 | 11/1998 | Athanikar | 424/440 |
| 5,846,557 | 12/1998 | Eisenstadt et al. | 424/439 |
| 5,854,267 | 12/1998 | Berlin et al. . | |
| 5,858,383 | 1/1999 | Precopio . | |
| 5,858,412 | 1/1999 | Staniforth et al. . | |
| 5,858,413 | 1/1999 | Jettka et al. . | |
| 5,858,423 | 1/1999 | Yajima et al. . | |
| 5,866,179 | 2/1999 | Testa | 426/3 |
| 5,877,173 | 3/1999 | Olney et al. | 514/217 |
| 5,882,702 | 3/1999 | Abdel-Malik et al. | 426/3 |
| 5,889,028 | 3/1999 | Sandborn et al. . | |
| 5,889,029 | 3/1999 | Rolf | 514/343 |

| | | | |
|---|---|---|---|
| 5,897,891 | 4/1999 | Godfrey | 426/74 |
| 5,900,230 | 5/1999 | Cutler | 424/49 |
| 5,912,007 | 6/1999 | Pan et al. | 424/440 |
| 5,912,030 | 6/1999 | Huziinec et al. | 426/3 |
| 5,916,606 | 6/1999 | Record et al. | 426/3 |
| 5,922,346 | 7/1999 | Hersh | 424/439 |
| 5,922,347 | 7/1999 | Hausler et al. | 424/441 |
| 5,928,664 | 7/1999 | Yang et al. | 424/440 |
| 5,958,380 | 9/1999 | Winston et al. | 424/48 |
| 5,958,472 | 9/1999 | Robinson et al. | 426/3 |
| 5,980,955 | 11/1999 | Grennberg et al. . | |
| 5,989,588 | 11/1999 | Korn et al. . | |
| 6,024,988 | 2/2000 | Ream et al. . | |
| 6,066,988 | 5/2000 | Gurol et al. . | |
| 6,090,412 | 7/2000 | Hashimoto et al. . | |

FOREIGN PATENT DOCUMENTS

| | | |
|---|---|---|
| 0239541 A2 | 9/1987 | (EP) . |
| 0371584 A2 | 6/1990 | (EP) . |
| 0 273 809 | 7/1998 | (EP) . |
| 2345938 | 3/1976 | (FR) . |
| 2 635 441 | 2/1990 | (FR) . |
| 2706771 | 6/1993 | (FR) . |
| 0 934 596 | 8/1963 | (GB) . |
| 0 963 518 | 7/1964 | (GB) . |
| 1 489 832 | 10/1977 | (GB) . |
| 2181646 A | 4/1987 | (GB) . |
| 0217487 | 7/1997 | (IT) . |
| 91-112450 | 9/1989 | (JP) . |
| 91-251533 | 11/1991 | (JP) . |
| 94-303911 | 11/1994 | (JP) . |
| 96-19370 | 1/1996 | (JP) . |
| 86/242561 | 10/1996 | (JP) . |
| 94-2868 | 4/1994 | (KR) . |
| 84/02271 | 6/1984 | (WO) . |
| 90/12511 | 11/1990 | (WO) . |
| 90/12583 | 11/1990 | (WO) . |
| 92/06680 | 4/1992 | (WO) . |
| 95/00038 | 1/1995 | (WO) . |
| 95/00039 | 1/1995 | (WO) . |
| 95/10290 | 4/1995 | (WO) . |
| 96/00070 | 1/1996 | (WO) . |
| 96/03975 | 2/1996 | (WO) . |
| 97/21424 | 6/1997 | (WO) . |
| 98/23165 | 6/1998 | (WO) . |
| 98/23166 | 6/1998 | (WO) . |
| 98/23167 | 6/1998 | (WO) . |
| 99/33352 | 7/1999 | (WO) . |
| 99/44436 | 9/1999 | (WO) . |
| 00/13523 | 3/2000 | (WO) . |

OTHER PUBLICATIONS

Adams, M.W., d–Alpha Tocopheryl Polyethylene glycol 1000 succinate (Eastman vitamin E TPGS) as an Emulsifier and Bioenhancer for Drugs and Lipophilic Compounds, 6th International Conference on Pharmaceutical Technology, Paris, Jun. 2–4, 1992.

Chang, Tammy et al., "The Effect of Water–Soluble Vitamin E on Cyclosporine Pharmacokinetics in Healthy Volunteers," Asbtract in American Society to Clinical Pharmacology and Therapeutics, 57(2):163, Feb. 1995.

Hebert, Mary F. et al.; "Bioavailability of Cyclosporine with Concomitant Rifampin Administration is Markedly Less Than Predicted by Hepatic Enzyme Induction" (1992) Clin. Pharmacol. Ther. 52:453–457.

Kronbach, Thomas et al.; "Oxidation of Midazolam and Triazolam by Human Liver Cytochrome P450IIIA4" (1989) Molec. Pharm. 36:89–96.

Lalka et al.,; "The Hepatic First–Pass Metabolism of Problematic Drugs" (1993) J. clin. Pharmacol. 33:657–669.

Lum et al.; "Clinical Trials of Modulation of Multidrug Resistance. Pharmacokinetic and Pharmacodynamic Considerations" (1993) Cancer 72:3502–3514.

Muranishi, Shozo; "Absorption Enhancers" (1990) Crit. Rev. Ther. Drug Carrier Sys., 7:1–33.

Somberg et al.; "The Clinical Implications of First–Pass Metabolism: Treatment Strategies for the 1990's" (1993) J. Clin. Pharmacol. 33:670–673.

Tam, Yun K.; "Individual Variation in First–Pass Metabolism" (1993) Clin. Pharmacokinet. 25:300–328.

Van Hoogdalem et al.; "Intestinal Drug Absorption Enhancement: An Overview" (1989) Pharmacol. Ther. 44:407–443.

Warren et al.; "Increased Accumulation of Drugs in Multidrug–Resistant Cell Induced by Liposomes" (1992) Cancer Research 52:3241–3245.

Watkins, Paul B.; "The Role of Cytochromes P–450 in Cyclosporine Metabolism" (1990) J.Am. Acad. Dermacol. 23:1301–1309.

Wrighton et al.; "In Vitro Methods for Assessing Human Hepatic Drug Metabolism: Their Use in Drug Development" (1993) 25:453–484.

Wu et al.; "Use of IV and Oral Drug Levels from Cyclosporene (CsA) with Concomitant Rifampin to Differentiate Gut Absorption an d Metabolism" (1993) Pharm. Res. 10: abstract ppdm8185.

Zamora et al.; "Physical–Chemical Properties Shared by Compounds that Modulate Multidrug Resistance in Human Loukemic Cells" (1988) Molec. Pharmacol. 33:454–462.

"Flavor Encapsulation Technologies, Flavor Unit Sweet, Product Management," H&R (undated) (published at least before Nov. 27, 1996), 25 pages.

Dr. Massimo Calanchi and Dr. Sam Ghanta, "Taste–masking of oral formulations", Eurand International SpA, Pharmaceutical, Manufacturing International, 1996 (5 pages).

The Eurand Group, Brochure (undated) (published at least before Nov. 27, 1996), (16 pages).

Merck Index, 11th Ed. #1635 "Caffeine" (1989), p. 248.

Merck Index, 12th Ed., #2337 "Cimetidine" (1996), p. 383.

Merck Index, 12th Ed., #3264 "Dimethicone" (1996), p. 544.

Merck Index, 12th Ed., #3972 "Famotidine" (1996), p. 667.

Merck Index, 12th Ed., #6758 "Nizatidine" (1996), p. 1143.

Merck Index, 12th Ed., #8286 "Ranitidine" (1996), p. 1395.

James G. Elliott, "Application of Antioxidant Vitamins in Foods and Beverages" Food Technology, (Feb., 1999), pp. 46–48.

C. Curtis Vreeland, "Nutraceuticals Fuel Confectionery Growth" Candy R&D, (Mar., 1999), pp. 29, 31–32, 34–35.

Kitty Broihier, R.D., "Foods of Tomorrow, Milking The Nutrition Market", Food Processing, (Mar., 1999), pp. 41, 42 and 44.

Kitty Broihier, R.D., "Tea Time For Nutraceuticals, New Black, Green Tea Products Brew Up a Bevy Of Health Benefits", Food Processing; (Mar., 1999), pp. 59, 61 and 63.

Andrea Allen, Jack Neff, Lori Dahm and Mary Ellen Kuhn, "Exclusive Guide to Wellness Foods and Nutraceuticals", Food Processing (Special Supplement), (Mar., 1999).

Product package "Aspergum" distributed by Heritage Consumer Products, LLC (on sale prior to Nov. 27, 1995).

Product package "Chew & Sooth Zinc Dietary Supplement Gum" by Gumtech International, Inc. (undated).

Product package "Dental Care the Baking Soda Gum" distributed by Church & Dwight Co., Inc. (1998).

Product package "BreathAsure Dental Gum" distributed by Breath Asure, Inc. (1998).

Product package "Trident Advantage with Baking Soda" distributed by Warner–Lambert Co. (1998).

Product package "CHOOZ Antacid/Calcium Supplement with Calcium Carbonate" distributed by Heritage Consumer Products Co.

Hertiage Consumer Products Co. article from the Internet "Cosmetics and Toiletries, The Heritage Story", printed Jul. 20, 2000, <http://www.cnewsusa.com/Connecticut/14997.html>, 1 page.

The United States Pharmacopeia The National Formulary—"General Information", dated Jan. 1, 1990 pp 1624–1625 and pp 1696–1697.

Gumtech article from the Internet "Customized Solutions For Consumer Brands", printed Oct. 18, 2000,<http://www.gum–tech.com/cus–brands.html>, 3 pages.

Product package for Stay Alert Caffeine Supplement Gum, distributed by Amurol Confections Company (first quarter 1998).

Rabeprazole article from the Internet "Rabeprazole: Pharmacokinetics and Safety in the Elderly", printed Sep. 22, 2000,<http://www.mmhc.com/cg/articles/CG9905/Hum–phries.html>, 2 pages.

\* cited by examiner

OVER-COATED CHEWING GUM FORMULATIONS INCLUDING TABLETED CENTER

This is a continuation-in-part of U.S. patent application Ser. No. 09/510,878, filed on Feb. 23, 2000, which is a continuation-in-part of U.S. patent application Ser. Nos. 09/286,818, filed on Apr. 6, 1999 and PCT Patent Application No. PCT/US99/29742 filed on Dec. 14, 1999.

BACKGROUND OF THE INVENTION

The present invention generally relates to the delivery of medicaments and other agents. More specifically, the present invention relates to the delivery of medicaments and agents using chewing gum formulations and methods for producing such products.

It is of course known to provide agents to individuals for various purposes. These agents can be used to treat diseases and as such are typically referred to as drugs or medicaments. Likewise, the drugs or medicaments can be used for prophylactic purposes. Still, it is known to provide agents to an individual for a variety of non-medical purposes including enhancing performance or maintaining or initiating alertness.

There are a great variety of such agents. These agents run the gamut from stimulants such as caffeine to drugs such as analgesics, tranquilizers, cardiovascular products, insulin, etc. Some such agents are taken on an as needed basis while other agents must be taken at regular intervals by the individual.

Typically, drugs (medicaments) are administered parenterally or enterally. Of course, parenteral administration is the administration of the drug intravenously directly into the blood stream. Enteral refers to the administration of the drug into the gastrointestinal tract. In either case, the goal of the drug administration is to move the drug from the site of administration towards the systemic circulation.

Except when given intravenously, a drug must traverse several semipermeable cell membranes before reaching general circulation. These membranes act as a biological barrier that inhibits the passage of drug molecules. There are believed to be four processes by which drugs move across a biological barrier: passive diffusion; facilitated diffusion; active transport; and pinocytosis.

Passive diffusion is the transport across the cell membrane wherein the driving force for the movement is the concentration gradient of the solute. In orally administered drugs, this absorption occurs in the small intestines. Facilitated diffusion is believed to be based on a carrier component that combines reversibly with the substrate molecule at the cell membrane exterior. The carrier substrate complex diffuses rapidly across the membrane with release of the substrate at the interior surface. Active transport requires an energy expenditure by the cell and appears to be limited to agents with structural similarities to normal body constituents. These agents are usually absorbed from specific sites in the small intestines. Pinocytosis refers to the engulfing of particulars or fluid by a cell. It is believed to play a minor role in drug transport. *Merck Manual*, 16th Edition, pp. 2598–2599.

In determining the efficacy of a drug and the effectiveness of the use of a drug to treat a disease, drug absorption is a critical concern. Drug absorption refers to the process of drug movement from the site of administration toward the systemic circulation.

Oral administration of drugs is by far the most common method. When administered orally, drug absorption usually occurs due to the transport of cells across the membranes of the epithelial cells within the gastrointestinal tract. Absorption after oral administration is confounded by numerous factors. These factors include differences down the alimentary canal in: the luminal pH; surface area per luminal volume; perfusion of tissue, bile, and mucus flow; and the epithelial membranes. See *Merck Manual* at page 2599.

A further issue effecting the absorption of orally administered drugs is the form of the drug. Most orally administered drugs are in the form of tablets or capsules. This is primarily for convenience, economy, stability, and patient acceptance. Accordingly, these capsules or tablets must be disintegrated or dissolved before absorption can occur. There are a variety of factors capable of varying or retarding disintegration of solid dosage forms. Further, there are a variety of factors that effect the dissolution rate and therefore determine the availability of the drug for absorption. See *Merck Manual* at page 2600.

Parenteral administration allows for the direct placement of the drug into the blood stream. This usually insures complete delivery of the dose to the general circulation. However, administration by a route that requires drug transfer through one or more biologic membranes to reach the blood stream precludes a guarantee that all of the drug will eventually be absorbed. Even with parenteral administration, because capillaries tend to be highly porous, the perfusion (blood flow/gram of tissue) is a major factor in the rate of absorption. Thus, the injection site can markedly influence a drugs' absorption rate; e.g., the absorption rate of diazepam injected IM into a site with poor blood flow can be much slower than following an oral dose. See *Merck Manual* at page 2601.

Not only is drug absorption an issue in drug delivery but also the bioavailability of the drug is also critical. Bioavailability is defined as the rate at which and the extent to which the active moiety (drug or metabolite) enters the general circulation, thereby gaining access to the site of action. Bioavailability depends upon a number of factors, including how a drug product is designed and manufactured, its physicochemical properties, and factors that relate to the physiology and pathology of the patient. See *Merck Manual* at page 2602.

When a drug rapidly dissolves from a drug product and readily passes across membranes, absorption from most site administration tends to be complete. This is not always the case for drugs given orally. Before reaching the vena cava, the drug must move down the alimentary canal and pass through the gut wall and liver, which are common sites of drug metabolism. Thus, the drug may be metabolized before it can be measured in the general circulation. This cause of a decrease in drug input is called the first pass effect. A large number of drugs show low bioavailability owing to an extensive first pass metabolism. The two other most frequent causes of low bioavailability are insufficient time in the GI tract and the presence of competing reactions. See *Merck Manual* at page 2602.

Bioavailability considerations are most often encountered for orally administered drugs. Differences in bioavailability can have profound clinical significance.

Although parenteral administration does provide a method for eliminating a number of the variables that are present with oral administration, parenteral administration is not a preferable route. Typically, parenteral administration requires the use of medical personnel and is just not warranted nor practical for the administration of most agents and drugs, e.g., analgesics. Even when required, parenteral administration is not preferred due to patient concerns including comfort, infection, etc., as well as the equipment and costs involved. However, despite best efforts certain therapies require parenterally injected drugs. For example, research for decades has focused on an attempt to deliver insulin to an individual through a non-parenteral means. Despite such efforts, today insulin is still only administered intravenously.

Thus, there is a need for an improved method of delivering drugs and agents to an individual.

In producing products for delivering medicaments and other agents to an individual, it may be critical that a predefined amount of medicament or agent is delivered per dose of the product. This allows the physician and/or patient to determine the amount of product to ingest and insure that a safe and effective level of medicament or agent is delivered. If the medicament or agent is located in a coating of the product it is necessary to ensure that definite levels of coating are present in each product. This requires a manufacturing process that allows for the accurate production of coated products.

SUMMARY OF THE INVENTION

The present invention provides improved methods for manufacturing products for delivering a medicament or agent to an individual as well as such products. To this end, a gum center is tableted and then coated to produce a coated chewing gum product including a medicament or agent. The medicament or agent is present within the coating or shell that substantially encloses the tableted gum center (the water soluble portion and insoluble base portion). It has been found that by tableting the gum center that a specifically defined coating can be provided, providing a predetermined and controllable level of medicament or agent.

Improved formulations including medicaments or agents are also provided by the present invention.

To this end, the present invention provides a coated chewing gum composition including a tableted gum center. The tableted gum center includes a water soluble portion and a water insoluble portion. The coating substantially surrounds the tableted gum center, the coating comprises at least 50% by weight of the chewing gum product. The coating includes a medicament or agent.

In an embodiment, the coating includes a sufficient amount of a masking agent to improve the organoleptic properties of the coating containing the medicament. The masking agent may be chosen from the group consisting of: sucralose; zinc gluconate; ethyl maltol; glycine; acesulfame-K; aspartame; saccharin; fructose; xylitol; spray dried licorice root; glycerrhizine; dextrose; sodium gluconate; glucono delta-lactone; ethyl vanillin; vanillin; normal and high-potency sweeteners; and a variety of appropriate flavors.

In an embodiment, the coating includes a high-intensity sweetener. In a further embodiment, the high-intensity sweetener is chosen from the group consisting of aspartame, sucralose, and acesulfame-K.

In an embodiment, the tableted gum center comprises approximately 15% to about 90% by weight water insoluble gum base.

In an embodiment, the coating comprises up to 75% by weight of the chewing gum composition.

In an embodiment, the coating is a recrystallized granular coating.

In an embodiment, the coating is an amorphous coating.

In an embodiment, the coating is a powder coating.

In an embodiment, the medicament is chosen from the group consisting of: analgesics; muscle relaxants; antacids; antihistamines; decongestants; anti-inflammatories; antibiotics; antivirals; psychotherapeutic agents; insulin; and cardiovascular agents.

In another embodiment of the present invention a method of drug delivery is provided. The method comprising the steps of: providing a chewing gum that includes a coating that comprises at least 50% by weight of the chewing gum, the coating including a medicament that substantially surrounds a tableted gum center; chewing the chewing gum to cause the medicament to be released from the chewing gum composition into the buccal cavity of the chewer; and continuing to chew the chewing gum thereby creating a fluid pressure causing the medicament to enter the systemic system of the chewer through the oral mucosa contained in the buccal cavity.

In a further embodiment of the present invention, a method for reducing the amount of agent necessary to achieve an effect in an individual as compared to a typical agent that is swallowed is provided. The method comprises the steps of: providing a chewing gum including a coating that surrounds a tableted gum center, the coating comprising at least 50% by weight of the total chewing gum, the coating including an agent that is typically swallowed by an individual to achieve a specific effect. However, the coating includes less than the typical amount of agent that is swallowed by the individual to achieve the effect; chewing the chewing gum and thereby causing the agent to be released into the salvia of the individual; and continuing to chew the chewing gum forcing the agent through the mucous membranes in a buccal cavity of the individual.

In an embodiment of the method, the agent is a medicament. In an embodiment of the method, the medicament is chosen from the group consisting of: analgesics; muscle relaxants; antihistamines; decongestants; antacids; anti-inflammatories; antibiotics; antivirals; psychotherapeutic agents; and cardiovascular agents.

In yet another embodiment of the present invention a method of delivering a medicament is provided. The method comprising the steps of: providing a chewing gum including a coating that comprises at least 50% by weight of the chewing gum and surrounds a tableted gum center and includes a medicament; and chewing the chewing gum for at least 2 minutes.

In a still further embodiment of the present invention a chewing gum composition is provided. The chewing gum includes a tableted gum center including a water soluble portion and a water insoluble portion, the water insoluble portion comprising at least 15% by weight of the gum center. The coating surrounds the tableted gum center and includes a medicament and comprising at least 50% by weight of the chewing gum. The coating includes a macrosweetener.

Moreover, in an embodiment of the present invention, a method of manufacturing a product containing a medicament or agent is provided. The method comprising the steps of: preparing a tableted gum center having water-soluble portion and a water-insoluble; coating the tableted center with a powder and a syrup to create a coated product, at least one of the powder or syrup portion including a medicament or agent; and the coated product comprising at least 50% by weight syrup and powder coating.

In an embodiment the powder and syrup are coated on the gum center in alternating steps until a sufficient coating has been built up.

In an embodiment the coating is not covered with a shellac or other finishing layer but rather maintains a matte finish.

Accordingly, an advantage of the present invention is to provide new methods for manufacturing products for delivering medicaments or agents to an individual.

Furthermore, an advantage of the present invention is to provide an improved product containing a medicament.

Still further, an advantage of the present invention is to provide a method of delivering medicaments to an individual that provides for increase absorption and bioavailability as compared to medicaments that are designed to be absorbed in the GI tract.

Further, an advantage of the present invention is to provide a method of administering a medicament or agent to an individual at a lower level than is typically administered orally while still achieving the same effect.

Furthermore, an advantage of the present invention is to provide a method for administering medicaments or agents to an individual that heretofore were administered parenterally.

Additionally, an advantage of the present invention is to provide a method for administering medicaments that is more palatable than current methods.

Another advantage of the present invention is to provide a method for manufacturing products including medicaments or agents in the coating.

Moreover, an advantage of the present invention is to provide an improved method for drug delivery.

Still, an advantage of the present invention is to provide a method for ensuring that a coated product that includes a medicament has a precise level of medicament.

An advantage of the present invention is that a coated product is provided wherein the coating can absorb or lose moisture without apparent degradation.

Further, an advantage of the present invention is that a coated chewing gum product including medicament is provided having an extended shelf-life.

Furthermore, an advantage of the present invention is that it can produce medicament-containing products having precise sizes and shapes.

Another advantage of the present invention is to provide a method of controlling the amount of agent containing coating that is used on a coated chewing gum product.

Additional features and advantages of the present invention will be described in and apparent from the detailed description of the presently preferred embodiments and the figures.

DETAILED DESCRIPTION OF THE PRESENTLY PREFERRED EMBODIMENTS

The present invention provides improved methods for delivering medicaments and other agents to an individual as well as improved products including such medicaments or agents and methods for producing same.

Pursuant to the present invention, a medicament or agent is contained in a coating that surrounds a tableted gum center formulation. As used herein "tableted" means that a gum center is provided that has a precise size (within an acceptable range) depending on the medicament or agent and shape. Thus allows an accurate control of the coating as well as allows one to create products having specific sizes and shapes. The coating comprises at least 50% by weight of the entire chewing gum product.

As the chewing gum is chewed, the medicament or agent is released into the saliva. During continual chewing, the medicament or agent in the saliva is then forced through the oral mucosa in the buccal cavity due to the pressure created by the chewing. The oral mucosa has a thin epithelium and a rich vascularity. Thus, the oral mucosa favors drug absorption. In contrast to a typically orally ingested drug, wherein the solution is in contact too briefly for absorption to be appreciable through the oral mucosa, it is believed that during chewing, the agent and/or medicament remains in the buccal cavity and is forced through the oral mucosa. Also it has been surprisingly found that an increase in the absorption of the drug is achieved as well as an increase in the bioavailability of the drug as compared to typical oral administration. It has been found that the drug or agent is absorbed much quicker than if it was swallowed as in a typical oral administration. Indeed, the absorption approaches that of a parenteral administration, and bioavailability is also much greater than oral administration.

Figure 1:
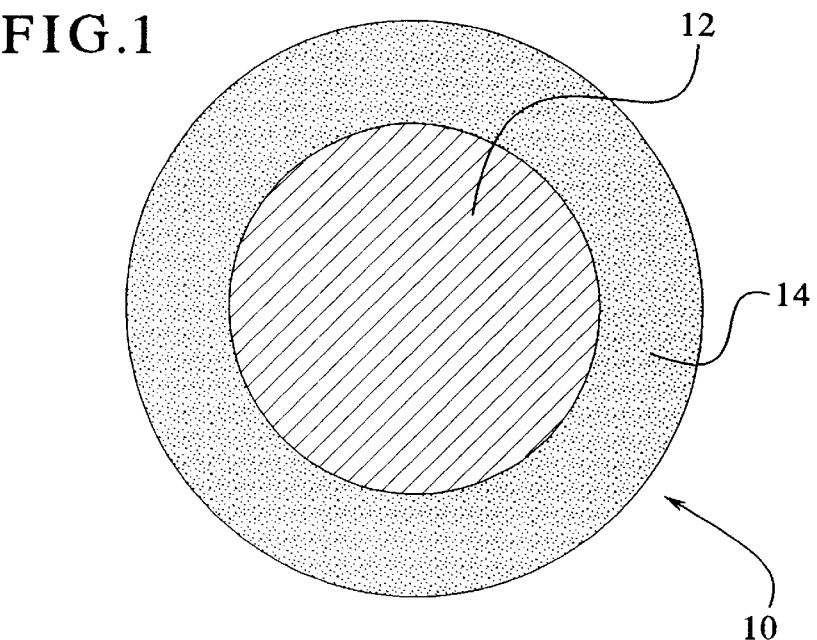
FIG. 1 illustrates generally an embodiment of the chewing gum of the present invention.
Figure 4:
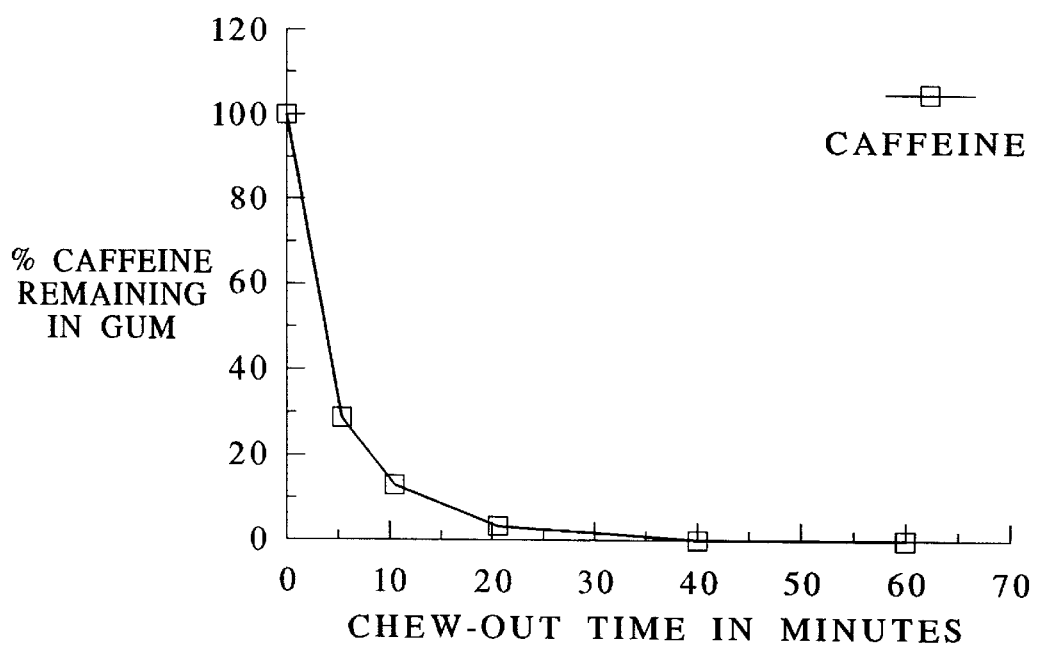
FIG. 4 illustrates graphically the results of Experiment No. 3 that is discussed supra.

Referring to FIG. 1, an embodiment of the chewing gum composition 10 of the present invention is illustrated. As illustrated, the chewing gum composition 10 includes a tableted gum center 12. The tableted gum center can be any chewing gum formulation known in the art, though as noted below preferably the tableted gum center has a higher level of water insoluble gum base than is typically used. Pursuant to the present invention, surrounding the tableted gum center 12 is a coating 14. The coating 14 includes a medicament or other active agent.

As noted above, the tableted gum center 12 can be any size or shape. However, the key is that by tableting the gum center, one can control to a precise relative standard deviation, the size of the gum center 12. This allows one to accurately control the amount of coating 14 that is placed around the gum center 12 to create the resultant product. In this regard, if the gum center is too large or too small, the resultant coating will either be greater or less than desired. Because the coating, as noted below, contains a medicament, if the size of the gum center 12 is not the predetermined size, the level of medicament present in the resultant product could vary. By precisely controlling the size of the gum center, through the tableting process, one is ensured that a precise level of coating, and therefore medicament, can be provided and thereby delivered.

Additionally, by using the tableting process one can vary the size and shape of the resultant product. For example, for a chewing gum product including an analgesic, the product can have an aspirin shape. In a similar vein, for proprietary designs that are used for certain drugs, one can create the gum center in the proprietary design allowing the resultant product to have the proprietary shape or design.

A variety of different tableting processes can be used. What is important is that a process is used that allows one to create a uniform gum center. For example, conventional drug tableting equipment or confectionary tableting product equipment can be utilized. An example of such equipment is the Stokes tableting machine available from Stokes Manufacturing Inc..

Referring now to the coating 14, the coating 14 comprises at least 50% by weight of the chewing gum composition.

Preferably, the coating 14 comprises approximately 50% to about 75% by weight of the chewing gum composition and in a preferred embodiment, the coating 14 comprises approximately 67% by weight of the product. A variety of coatings can be utilized. For example, the coating can be a soft amorphous coating. Or, the coating can be a recrystallized granular coating. As discussed below, in a preferred embodiment, the coating is applied as a syrup/powder composition.

Preferably, the coating 14 will include masking agents. In this regard, high-intensity sweeteners and appropriate flavors can be used to mask any off notes that are present due to the medicament or agent. It has been found that with respect to certain medicaments or agents that may have an astringent or bitter taste that by adding a masking agent to the formulation, that a much more palatable formulation, including the medicament, can be provided. In this regard, even though the medicament in for example, its powder form may be bitter or have an offensive taste, the matrix used as the coating of the present invention, including the masking agent, will afford a product having acceptable organoleptic properties. For example, it has been surprisingly found that by solubilizing a powdered matrix of medicament and masking agent, this increases the ability of the masking agent to cover up bitter and bad flavors produced by the medicament or agent. By selecting specific masking agents based on the bad or off taste produced by the medicament, one can provide a palatable formulation.

For example, if one is attempting to cover an astringent flavor such as aspirin, one could use masking agents found to be effective against astringency such as fructose and high-intensity sweeteners, e.g. saccharin, aspartame, sucralose, and acesulfame-k. In the case of a moderately bitter active ingredient, such as caffeine, one would use ingredients such as glycine, ethyl maltol, zinc gluconate, licorice root powder, high-intensity sweeteners, etc. In the case of a very bad tasking active ingredient such as acetaminophen it has been found that peppermint functions very well, but, may need to be augmented with a high-intensity sweetener, such as, for example, aspartame.

The masking agents, in an embodiment, are selected from the group consisting of: sucralose; zinc gluconate; ethyl maltol; glycine; acesulfame-k; aspartame; saccharin; fructose; xylitol; maltitol; isomalt; salt; spray dried licorice root; glycyrrhizin; dextrose; sodium gluconate; sucrose; glucono delta-lactone; ethyl vanillin; and vanillin.

In an embodiment of the invention, sufficient masking agent will be used in the coating to improve and provide acceptable organoleptic properties to the chewing gum product. As used herein to provide "acceptable organoleptic properties" means that the chewing gum formulation will have a sufficiently pleasant, or at least non-offensive taste, to allow the consumer to chew the chewing gum for at least two minutes. Whether a masking agent is necessary and/or the amount of masking agent will vary depending on medicament or agent. Of course, if desired, more than one masking agent can be used, e.g., zinc gluconate and a sweetener or flavor. In an embodiment, the masking agent may comprise approximately 30% to about 99% by weight of the coating formulation.

In a preferred embodiment, the coating includes a high-intensity sweetener such as aspartame, sucralose, and acesulfame-k. Preferably, the high-intensity sweetener comprises approximately 0.5% to about 5% by weight of the coating.

As noted above, the coating will include a medicament or agent. It has also been surprisingly found that less medicament or agent can be placed in the chewing gum than is typically orally administered to an individual to achieve an effect and the same bioequivalence can be achieved. In fact, it has been surprisingly found that in certain instances, for at least certain drugs and agents, the administration of the medicament or agent using chewing gum through the buccal cavity can provide an increase effect even as compared to parenteral administration.

For example, caffeine is commonly used as a stimulant to alleviate the effects of sleep deprivation. It is almost completely metabolized in the liver and therefore classified as a low clearance, flow independent drug. This means its rate of inactivation is unaffected by delivery to the liver and can only be modified by a change in the hepatic enzyme activity.

The pharmacokinetics of caffeine have been well documented and there is no significant difference between oral and intravenous administration. However, data set forth in detail below, suggests that the absorption rate constant (Ka) is significantly increased when caffeine is administered through chewing gum. This means that the caffeine is moving into the systemic circulation at a significantly faster rate. A similar change in the onset of dynamic response has also been noted, e.g., alertness and performance.

It has additionally been surprisingly found that for at least certain agents that placing the agent in the chewing gum can have a triggering effect on the agent that may be in the systemic circulation. For example, it has been found that with respect to caffeine that is ingested orally, that after the ingestion of a certain amount of caffeine, and the elapse of a certain period of time, that further ingestion of caffeine has a negligible effect on the individual. However, upon chewing gum with caffeine there has been observed a triggering effect that appears to create a synergistic effect with the caffeine that is in the systemic circulation. It is believed that this triggering effect will also be present with other agents, e.g., analgesics.

It is envisioned, that a variety of different medicaments and agents can be placed in the coating. For example, such agents include, inter alia, stimulants such as caffeine. Generally, such medicaments include, inter alia, analgesics, antibiotics, antivirals, antihistamines, anti-inflammatories, decongestants, antacids, muscle relaxants, psychotherapeutic agents, insulin, and cardiovascular agents. It is envisioned, that depending on the medicament, the resultant chewing gum can be used to treat, inter alia: coughs; colds; motion sickness; allergies; fevers; pain; inflammation; sore throats; cold sores; sinus problems; diarrhea; diabetics; depression; anxiety; and other maladies and symptoms. Specific agents/medicaments include, by way of example and not limitation: caffeine; aspirin; acetaminophen; ibuprofen; hydroxycitric acid; chromium picolinate; phosphatidylserine; nicotine; insulin; Echinacea purpurea; zinc; vitamin C; ginseng; kola nut; kaua kaua; and chamomile.

Preferably, the agents or medicaments are contained in the coating of the chewing gum formulation at levels of approximately 50 micrograms to 500 milligrams. The specific levels will depend on the active ingredient. For example, if chromium picolinate is the active ingredient in an embodiment, it would be present at a level of 50 micrograms per serving (2.8 grams of coated chewing gum); aspirin would be preset at a level of 325 milligrams per 2.8/gram serving. The level of medicament or agent in the coating of the chewing gum formulation is selected so as to create, when the gum is chewed, a sufficiently high concentration of the medicament or agent in the saliva.

For example, when the agent is a stimulant such as nicotine or caffeine, the level of the stimulant in the coating of the chewing gum should be such that it creates a saliva content of stimulant of approximately 15 to 440 ppm when the chewing gum is chewed for 2 minutes. At this level, a sufficient amount of stimulant will be delivered to the chewer to create the effects set forth in the application. If a medicament is used such as a medicinal (e.g., analgesics), sufficient medicinal should be present in the coating of the chewing gum to create a salvia content of approximately 1700 to approximately 4400 ppm after the chewing gum has been chewed for 2 minutes. For a botanicals (e.g., chamomile, kava, kola, nut, ginseng, and Echinacea), the agent should be present in a sufficient amount to create a saliva content of approximately 85 to 1100 ppm when the chewing gum is chewed for 2 minutes. For a metabolizer, for example, chromium picolineate and hydroxi-chitic acid, the agents should be present in an amount to create a saliva content of approximately 0.5 to about 900 ppm when chewed for at least two minutes. If the agent is a vitamin or mineral (e.g., phosphatidy serine, vitamin C, and zinc), the agent should be present in the amount to create a saliva content of the vitamin or mineral of approximately 10 to about 250 ppm when chewed for 2 minutes.

Pursuant to the present invention, depending on the agent or medicament, the dosing regiment will change. For example, if the medicament is an analgesic, the chewing gum would be taken on an as needed basis. Of course, similar to the oral administration of an analgesic, there would be restrictions on the number of pieces of chewing gum, chewed, for example, not more often than one stick every four hours and not more often than four to five times a day.

If the agent is a stimulant such as caffeine to be used to enhance performance than the chewing gum would be chewed, in a preferred embodiment ten minutes or less before the performance. As set forth below in the experiment, it has been surprisingly found that for a chewing gum stick including caffeine, with another 5 minutes of chewing a high level of alertness is achieved.

A variety of methods can be used for constructing the coating of the chewing gum. Typically coatings are applied to chewing gum in a three-phase operation. In this regard, the first phase is to add a crude coating of an alternate application of syrup and powder is applied. This is followed by a second phase called the finishing coating in which finer powder and longer tumbling is used to produce a smooth finish. Finally a shellacking and polishing third phase is performed to provide a high-sheen smooth finish. In a preferred embodiment, the second phase is not used and the third phase is optional. As noted above, in contrast to typical coated chewing gum products, the products of the present invention include at least 50% to 75% by weight coating. Using only the first phase of the method, this large percent of coating can be applied to the product in a realistic time-frame.

In an embodiment, the coating comprises approximately 10 to about 30% by weight syrup and approximately 70% to about 90% by weight powder. For example, in a preferred embodiment, the coating comprises 20% syrup and 80% powder.

In an embodiment of constructing the coated chewing gum, first the syrup is distributed on the gum center. Then a portion of the powder is sprinkled on top to dry up the syrup. A further amount of syrup is added and powder supplied. This process is continued until the necessary amount of syrup and powder have been applied to the exterior of the chewing gum, e.g., 10 to 20 coating layers or more are applied. The coating which plays an important role as the masking agent, can include a combination of sugar, corn syrups, or in the case of a sugar-free product, various combinations of sugar alcohols, monomers, and polymers.

It has been found that by using this type of gross up coating process that advantages are achieved for the product containing medicament of the present invention. This is true whether or not the medicament is contained in the powder or in the syrup. Accordingly, if desired, the medicament can be contained in the syrup rather than in the powder.

Pursuant to the present invention, the coated product may not include a shellac or other finishing or shiny layer. It has been found, that the coating can comprise merely a matte finish and still function, not only satisfactorily, but has some advantages. In this regard, typically coated products that retain moisture on the coating along with a shellac layer may degrade due to moisture in the coating and therefore do not have an extended shelf-life. This is especially true with the thick coatings of the present invention. Such thick coatings absorb more moisture than thinner coatings. If a matte finish is utilized, although the thick coating layer can absorb the moisture, the matte finish allows the moisture to move into and out of the coating layer. This thereby prevents degradation of the product. Thus, the present invention provides a product having a thick coating with increased shelf-life.

The matte finish additionally not only allows a thick coating to be used but also ingredients that have high moisture absorption. Due to the matte finish, high moisture absorbing medicaments can be used without undue product degradation.

In an embodiment of the coating, dextrose or sucrose or combinations thereof function as the main ingredient. In a preferred embodiment, dextrose is utilized and the dextrose comprises approximately 50 to about 90% of the coating. The active ingredients or medicaments, in the coating may comprise as much as 30% of the coating down to very small amounts as long as the medication is efficacious. In a preferred embodiment, the flavors are powdered flavors and can range from 0.1% to approximately 5%. High-intensity sweeteners such as aspartame, sucralose, and acesulfame-k can also be used in the coating and range from approximately 0.5 to about 5% of the coating. As noted above, these high-intensity sweeteners are excellent masking agents.

The coating including medicament or agent can surround a variety of different gum center compositions. Referring now to the chewing gum center, pursuant to the present invention, the gum center may be based on a variety of different chewing gums that are known. For example, the gum center can be low or high moisture, sugar or sugarless, wax containing or wax free, low calorie (via high base or low calorie bulking agents), and/or may contain dental agents.

Chewing gum generally consists of a water insoluble gum base, a water soluble portion, and flavor. The water soluble portion dissipates with a portion of the flavor of the gum over a period of time during chewing. The gum base portion is retained in the mouth throughout the chew.

The insoluble gum base generally comprises elastomers, resins, fats and oils, softeners and inorganic fillers. The gum base may or may not include wax. Typically, gum base comprises approximately 20 to about 40% of the gum product. However, because in the present invention such a high level of coating is used, the gum center is unusually small; otherwise the entire coating chewing gum piece would be too large for consumption. If a typical amount of gum base was used in the small gum center, it would result in an inadequate cud to masticate. Consequently, in the present invention, the base level is higher than normal. The insoluble gum base can constitute approximately 30% to about 90% by weight of the chewing gum, in an embodiment, the gum base comprises at least 50% of the chewing gum.

In an embodiment, the chewing gum base of the present invention contains about 20% to about 60% by weight synthetic elastomer, about 0% to about 30% by weight natural elastomer, about 5% to about 55% by weight elastomer plasticizer, about 4% to about 35% by weight filler, about 5% to about 35% by weight softener, and optional minor amounts (about 1% or less by weight) of miscellaneous ingredients such as colorants, antioxidants, etc.

Synthetic elastomers may include, but are not limited to, polyisobutylene with GPC weight average molecular weight of about 10,000 to about 95,000, isobutylene-isoprene copolymer (butyl elastomer), styrene-butadiene, copolymers having styrene-butadiene ratios of about 1:3 to about 3:1, polyvinyl acetate having GPC weight average molecular weight of about 2,000 to about 90,000, polyisoprene, polyethylene, vinyl acetate-vinyl laurate copolymer having vinyl laurate content of about 5% to about 50% by weight of the copolymer, and combinations thereof.

Preferred ranges for polyisobutylene are 50,000 to 80,000 GPC weight average molecular weight and for styrene-butadiene are 1:1 to 1:3 bound styrene-butadiene, for polyvinyl acetate are 10,000 to 65,000 GBC weight average molecular weight with the higher molecular weight polyvinyl acetates typically used in bubble gum base, and for vinyl acetate-vinyl laurate, vinyl laurate content of 10–45%.

Natural elastomers may include natural rubber such as smoked or liquid latex and guayule as well as natural gums such as jelutong, lechi caspi, perillo, sorva, massaranduba balata, massaranduba chocolate, nispero, rosindinha, chicle, gutta hang kang, and combinations thereof. The preferred synthetic elastomer and natural elastomer concentrations vary depending on whether the chewing gum in which the base is used is adhesive or conventional, bubble gum or regular gum, as discussed below. Preferred natural elastomers include jelutong, chicle, sorva and massaranduba balata.

Elastomer plasticizers may include, but are not limited to, natural rosin esters such as glycerol esters or partially hydrogenated rosin, glycerol esters of polymerized rosin, glycerol esters of partially dimerized rosin, glycerol esters of rosin, pentaerythritol esters of partially hydrogenated rosin, methyl and partially hydrogenated methyl esters of rosin, pentaerythritol esters of rosin; synthetics such as terpene resins derived from alpha-pinene, beta-pinene, and/or d-limonene; and any suitable combinations of the foregoing. The preferred elastomer plasticizers will also vary depending on the specific application, and on the type of elastomer which is used.

Fillers/texturizers may include magnesium and calcium carbonate, ground limestone, silicate types such as magnesium and aluminum silicate, clay, alumina, talc, titanium oxide, mono-, di- and tri-calcium phosphate, cellulose polymers, such as wood, and combinations thereof.

Softeners/emulsifiers may include tallow, hydrogenated tallow, hydrogenated and partially hydrogenated vegetable oils, cocoa butter, glycerol monostearate, glycerol triacetate, lecithin, mono-, di- and triglycerides, acetylated monoglycerides, fatty acids (e.g. stearic, palmitic, oleic and linoleic acids), and combinations thereof.

Colorants and whiteners may include FD&C-type dyes and lakes, fruit and vegetable extracts, titanium dioxide, and combinations thereof.

The base may or may not include wax. An example of a wax-free gum base is disclosed in U.S. Pat. No. 5,286,500, the disclosure of which is incorporated herein by reference.

In addition to a water insoluble gum base portion, a typical chewing gum composition includes a water soluble bulk portion and one or more flavoring agents. The water soluble portion can include bulk sweeteners, high-intensity sweeteners, flavoring agents, softeners, emulsifiers, colors, acidulants, fillers, antioxidants, and other components that provide desired attributes.

Softeners are added to the chewing gum in order to optimize the chewability and mouth feel of the gum. The softeners, which are also known as plasticizers and plasticizing agents, generally constitute between approximately 0.5% to about 15% by weight of the chewing gum. The softeners may include glycerin, lecithin, and combinations thereof. Aqueous sweetener solutions such as those containing sorbitol, hydrogenated starch hydrolysates, corn syrup and combinations thereof, may also be used as softeners and binding agents in chewing gum.

Bulk sweeteners include both sugar and sugarless components. Bulk sweeteners typically constitute about 5% to about 95% by weight of the chewing gum, more typically, about 20% to about 80% by weight, and more commonly, about 30% to about 60% by weight of the gum. Sugar sweeteners generally include saccharide-containing components commonly known in the chewing gum art, including but not limited to, sucrose, dextrose, maltose, dextrin, dried invert sugar, fructose, levulose, glactose, corn syrup solids, and the like, alone or in combination. Sugarless sweeteners include, but are not limited to, sugar alcohols such as sorbitol, mannitol, xylitol, hydrogenated starch hydrolysates, maltitol, and the like, alone or in combination.

High-intensity artificial sweeteners can also be used, alone or in combination, with the above. Preferred sweeteners include, but are not limited to, sucralose, aspartame, salts of acesulfame, altitame, saccharin and its salts, cyclamic acid and its salts, glycerrhizinate, dihydrochalcones, thaumatin, monellin, and the like, alone or in combination. In order to provide longer lasting sweetness and flavor perception, it may be desirable to encapsulate or otherwise control the release of at least a portion of the artificial sweetener. Such techniques as wet granulation, wax granulation, spray drying, spray chilling, fluid bed coating, coacervation, and fiber extension may be used to achieve the desired release characteristics.

Combinations of sugar and/or sugarless sweeteners may be used in chewing gum. Additionally, the softener may also provide additional sweetness such as with aqueous sugar or alditol solutions.

If a low calorie gum is desired, a low caloric bulking agent can be used. Examples of low caloric bulking agents include: polydextrose; Raftilose, Raftilin; Fructooligosaccharides (NutraFlora); Palatinose oligosaccharide; Guar Gum Hydrolysate (Sun Fiber); or indigestible dextrin (Fibersol). However, other low calorie bulking agents can be used.

A variety of flavoring agents can also be used, if desired. The flavor can be used in amounts of about 0.1 to about 15 weight percent of the gum, and preferably, about 0.2% to about 5% by weight. Flavoring agents may include essential oils, synthetic flavors or mixtures thereof including, but not limited to, oils derived from plants and fruits such as citrus oils, fruit essences, peppermint oil, spearmint oil, other mint oils, clove oil, oil of wintergreen, anise and the like. Artificial flavoring agents and components may also be used.

Natural and artificial flavoring agents may be combined in any sensorially acceptable fashion.

A process for preparing the tableted gum center is as follows: to an unheated gum mixer, preferably a double sigma blade, shredded gum base is added. Along with the gum base is added powdered color and one-third of the portion of sugar that will be used. Mixing is begun in the gum mixer. After the sugar incorporates into the gum base, approximately 5–7 minutes, the second one-third portion of the sugar is added thereto. Once the mixture appears to be homogenous the remaining sugar portion (last third) is added. The total mixing time is approximately 25 minutes. The powder is removed from the mixer. The powder is shifted to desired mesh size. An appropriate amount of spray dried flavor, acid, tableting agents (magnesium stearate) and flow agents (silicone dioxide) are added. This is then mixed until the powder is homogenous. The resulting powder is then pressed on a tableting machine, for example, a Stokes machine.

By way of example, and not limitation, examples of some coated chewing gum formulations including a medicament or agent are as follows:

TABLETED COATED PRODUCT
The tableted gum will include a gum center and a coating. In an embodiment, the gum center will include the following ingredients in the following ranges:

| Ingredient | Range |
|---|---|
| Gum Base (powdered gum) | 15 to 90% |
| Powdered Sugar | 5 to 95% |
| Color (Lake) | 0 to 1% |
| S.D. Flavor | 0.1 to 10% |
| Magnesium Stearate | 0.1 to 5% |
| Silicon Dioxide | 0.1 to 5% |
| Macro-sweetener | 0.1 to 5% |

An embodiment of the tableted coated product is as follows:

| Tableted Gum Center | | Coating | |
|---|---|---|---|
| Ingredient | Wt. Percent | Ingredient | Grams |
| Gum Base (powdered gum) | 18.04 | Acetaminophen | 0.3490 |
| Powdered Sugar | 76.99 | Peppermint Flavor (dry) | 0.0072 |
| Color (Lake) | 0.01 | Menthol Flavor (dry) | 0.0062 |
| S.D. Flavor | 1.46 | Dextrose | 1.4200 |
| Magnesium Stearate | 1.50 | Sucrolose | 0.0030 |
| Silicon Dioxide | 1.00 | Aspartame | 0.0062 |
| Macro-sweetener | 1.00 | Glucose | 0.2080 |
| | 100.00% | | 2.0000 g |

ACETAMINOPHEN COATED BUBBLE GUM

| Ingredient | Grams |
|---|---|
| *Gum Center (1 gram)* | |
| Gum Base | 400.0 |
| Corn Syrup | 91.0 |
| Glycerine | 49.0 |
| Sugar | 829.9 |
| Red Dye | 0.7 |
| Aspartame | 14.0 |
| Bubble Gum Flavor | 15.4 |
| | 1400.0 |
| *Coating (1 gram)* | |
| Acetaminophen | 80.0 |
| Encapsulated Aspartame | 20.0 |
| Aspartame | 50.0 |
| Salt Flour | 2.5 |
| Dextrose | 643.5 |
| Bubble Gum Flavor | 4.0 |
| | 800.0 |

ACETAMINOPHEN COATED CHEWING GUM

| Ingredient | Grams |
|---|---|
| *Gum Center (1 gram)* | |
| Xylitol | 56.0 |
| Natural Peppermint Flavor | 27.0 |
| Natural Peppermint Flavor | 25.0 |
| Natural Menthol | 9.0 |
| Natural Peppermint Flavor | 26.0 |
| Glycerine 96% USP | 14.0 |
| Bubble Gum | 480.0 |
| Firm Modifier | 90.0 |
| Aspartame | 6.0 |
| Ace-K | 9.0 |
| Gum Base | 620.0 |
| Corn Syrup | 112.0 |
| Powdered Sugar | 406.0 |
| | 1400.0 |
| *Coating (2 grams)* | |
| Acetaminophen | 335.0 |
| Natural Peppermint | 7.0 |
| S.D. Menthol | 6.0 |
| Dextrose | 1,221.0 |
| Aspartame | 32.0 |
| | 1,601.0 |

PSEUDOEPHEDRIN COATED GUM

| Ingredient | Grams |
|---|---|
| *Gum Center (1 gram)* | |
| Xylitol | 56.0 |
| Natural Peppermint Flavor | 27.0 |
| Natural Peppermint Flavor | 25.0 |
| Natural Menthol | 9.0 |
| Natural Peppermint Flavor | 26.0 |
| Glycerine 96% USP | 14.0 |
| Gum Base | 670.0 |
| Firm Modifier | 90.0 |
| Aspartame | 6.0 |
| Ace-K | 9.0 |

-continued

PSEUDOEPHEDRIN COATED GUM

| Ingredient | Grams |
|---|---|
| Gum Base | 140.0 |
| Corn Syrup | 112.0 |
| Powdered Sugar | 406.0 |
| | 1,400.0 |
| Coating (2 grams) | |
| Dextrose | 1,476.00 |
| Eucalyptus* | 2.00 |
| Menthol* | 30.00 |
| Aspartame | 32.00 |
| Pseudoephedrin | 60.00 |
| | 1,600.00 |

*sprayed dried

PEPPERMINT CAFFEINE COATED CHEWING GUM

| Ingredient | Grams |
|---|---|
| Gum Center (1 gram) | |
| Xylitol | 56.0 |
| Natural Peppermint Flavor | 27.0 |
| Natural Peppermint Flavor | 25.0 |
| Natural Menthol | 9.0 |
| Natural Peppermint Flavor | 26.0 |
| Glycerine 96% USP | 14.0 |
| Gum Base | 620.0 |
| Firm Modifier | 90.0 |
| Aspartame | 6.0 |
| Ace-K | 9.0 |
| Gum Base | 140.0 |
| Corn Syrup | 112.0 |
| Powdered Sugar | 406.0 |
| | 1,400.0 |
| Coating (2 grams) | |
| Caffeine | 100.0 |
| Peppermint | 13.0 |
| Dextrose | 1,455.0 |
| Aspartame | 32.0 |
| | 1,600.0 |

By way of example, and not limitation, experiments and examples testing chewing gum including a medicament or agent in the gum body or coating are as follows:

Experiment No. 1

Single dose, placebo controlled, randomized, two-way crossover study in 20 subjects to evaluate the effect of 50 mg caffeine gum compared to placebo gum-on positive and negative mood affects. Healthy subjects 18–65. Screening questionnaire to evaluate average caffeine consumption, tobacco drug and alcohol status. Any subjects taking medications with a CNS affect were excluded from the study. Approximately 2 hours on two occasions separated by at least 24 hours.

Dosing: 1×stick of caffeine gum to be chewed for 30 minutes. The chewing gum had the formulation set forth above in the table entitled caffeine gum.

The subjects were instructed that they were to have caffeine, alcohol or other drug use for at least 8 hours prior to test. No tobacco products for at least 2 hours prior to test. Subjects must have been awake and active for at least 8 but no more than 16 hours prior to starting the test. Subjects will be required to complete a 10 part questionnaire at the following time points (−20, −10, −5 and at 2, 5, 10, 15, 20, 30, 40 and 1 hour after starting to chew the gum. Appropriate analysis of comparison of each individual item of the test and grouped analysis for both positive and negative affect.

Data was corrected for baseline data (−5 minute reading) at each time point. Means and standard deviations for both active and placebo groups were evaluated for all time points.

Figure 2:
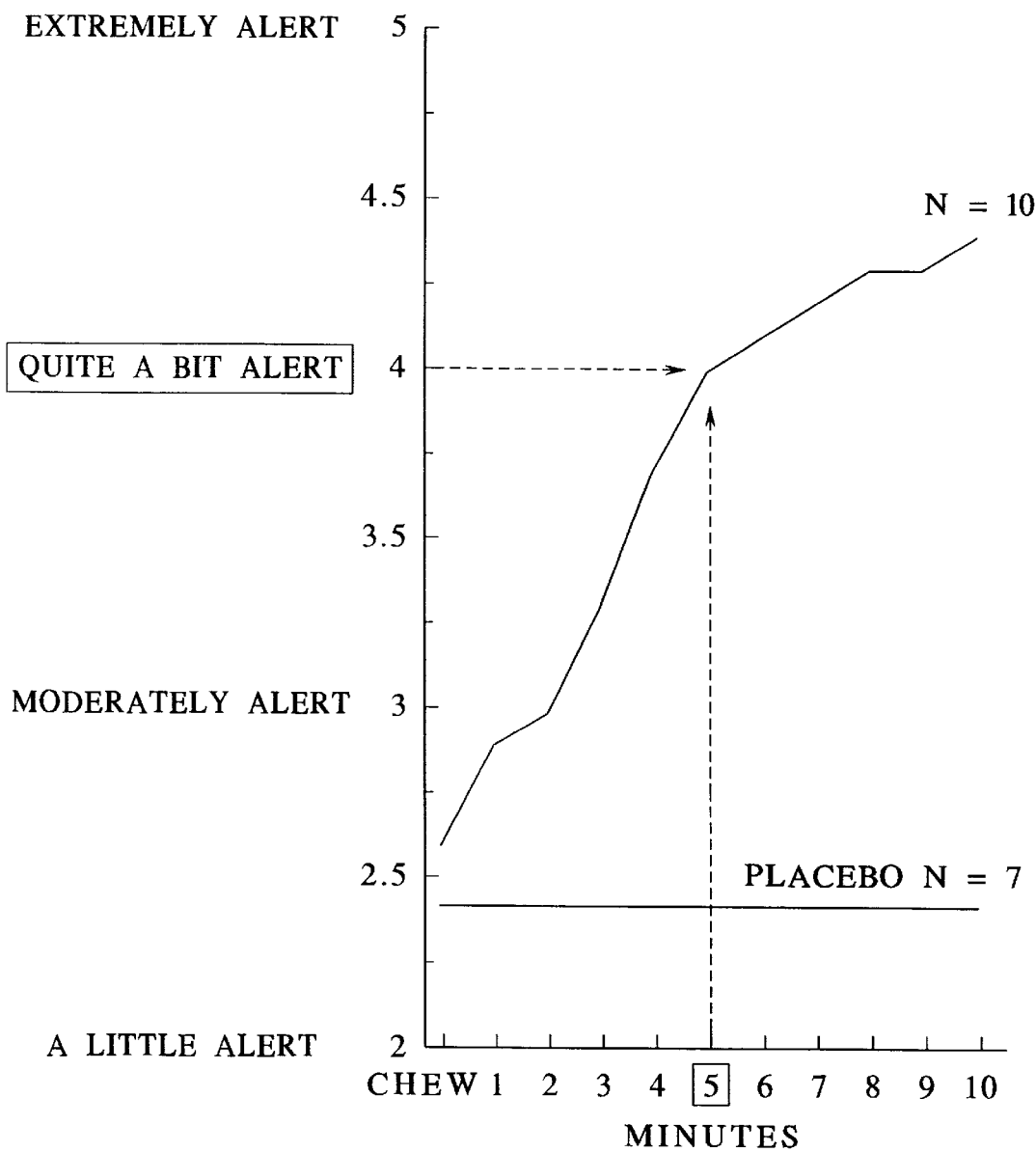
FIG. 2 illustrates graphically the results of Experiment No. 1 that is discussed supra.

The results of the analysis are set forth in FIG. 2. FIG. 2 graphically illustrates alertness versus time. These results demonstrate that by 5 minutes the subject reported that they were quite a bit alert. The alertness response was based on reference Panas feeling and emotion scale.

Experiment No. 2

A randomized, single-dose, two-way crossover study was conducted with six (6) healthy, adult, non-tobacco-using male subjects. A single 100 mg does of caffeine was administered in each study period after an overnight fast. The test treatment was two 50 mg caffeine chewing gum pieces (sticks), which were chewed for 15 minutes and removed. The reference treatment was one 100 mg chewable No-Doz® tablet, which was chewed and swallowed. One of the treatments was given in each period; the order of administration was according to the dosing randomization schedule. There was a 7-day washout between treatments.

Blood samples were collected pre-dose and over 15 hours after each dose. Plasma concentrations of caffeine were measured by a fully validated chromatographic procedure. Samples from subject with measurable pre-dose levels of caffeine were corrected for these levels. Pharmacokinetic parameters were calculated from the adjusted data and statistical analyses were performed to compare the test and reference treatments.

Clinical Procedures

A. Subject Selection

The 6 subjects who participated in this study were healthy males, in the age range of 25 to 35 years, and within 15% of their ideal weight as specified in the protocol.

All subjects were selected based on the absence of any clinically significant findings on the medical history, physical examination, and clinical laboratory evaluations. Any laboratory value or vital sign measurement more than 10% outside the normal range was evaluated individually by the investigator. All were determined to be not clinically significant for those subjects enrolled in the study. All screening evaluations were performed within 28 days of initial dosing.

B. Drug Supplies

Formulations:
  Test (A)—Two 50 mg chewing gum sticks, Amurol Confections Co. (Lot #ALRT7/9/19/96, No exp. Date)
  Reference (B)—One 100 mg No-Doz® chewable table, Bristo-Myers Products (Lot #601041, Exp. date October 1998).

Administration: The subjects received the test and reference after an overnight fast. The subjects randomized to the test first drank 240 ml of room temperature tap water. The chewing gum pieces were then chewed for 15 minutes and deposited into a labeled vial. The subjects randomized to the reference chewed the No-Doz® tablets and then drank 240 ml of room temperature tap water. The order of treatment administration was according to the randomization schedule.

All doses were administered at one-minute intervals beginning at 0700 hours. A thorough mouth check was performed to ensure that the chewable tablet was swallowed. A schedule of the actual dosing times, dates and treatment assignments is included in Table C2. All subjects remained under observation sitting upright or standing for at least two hours after each dosing. Six subjects were dosed in both Period I and Period II.

C. Study Conduct

Confinement, Meals: During the confinement periods of this study, the subjects were housed and fed at the clinical facility.

In each period, the subjects reported for check-in (Day −1) at least 12 hours before dosing. Meals were provided on check-in day and completed at least 10 hours prior to scheduled dosing time. No food or beverages (except water) were permitted after 2100 hours on Day −1.

During confinement (Day 1), standardized, caffeine-free meals or snacks were served at 4, 10 and 14 hours after dosing, as specified on the Activity Schedule and Menu found in Section 3. The same menu was used during each study period. The subjects consumed at least 95% all food and beverages that were required. The subjects were released from the clinical facility approximately 2200 hours after dosing in each study period. A 7-day washout separated the dosings.

Restrictions: Prior to check-in for the study, the subjects were instructed to take no prescribed medications for at least 14 days prior to the initial dosing and throughout the study. No over-the-counter medications were permitted for 72 hours before dosing in each study period. No medications were permitted during confinement except those administered. Subjects were also instructed to abstain from any products containing alcohol or caffeine for 48 hours prior to dosing and throughout each confinement. None of the subjects reported taking any restricted substance within the time frame indicated.

During the confinement periods of the study, water was restricted from one hour before until one hour after dosing except for water (240 ml) administered with the dose. Water was permitted ad lib at all other times. Subjects remained sitting upright or standing for 2 hours after each dosing, except as required for study procedures. No strenuous physical exercise was permitted during confinement.

Safety: Urine drug screens were performed at each check-in to test for alcohol, marijuana and cocaine metabolites.

Blood pressure (sitting), pulse rate, respiratory rate and oral temperature were measured before each dosing. The investigator considered the measurements of all subjects as clinically acceptable for dosing.

Blood pressure and pulse rate measurements (sitting) were obtained approximately one hour after each dose and prior to release in each study period to monitor the health of the subjects. Measurements were repeated if clinically warranted.

A blood sample was collected at the time of the last sample of the study for a hematocrit determination. All hematocrit values were within 10% of the normal range (41–50%).

Adverse Events: The subjects were monitored throughout the study for any adverse experiences. They were encouraged to report signs, symptoms, and any changes in health to the study nurse. None of the subject reported any adverse events during this study.

Pharmacokinetic Samples: In each period, blood samples were collected prior to dosing and at the following nominal times after dosing: 0.25, 0.5, 1, 1.5, 2, 2.5, 3, 4, 6, 8, 10, 12 and 15 hours. The samples were labeled at the time of collection with a unique 6-digit code number. Pre-dose samples were collected within 30 minutes before dosing. All plasma samples were stored frozen between −18° C. and −20° C. until transfer to the laboratory for analysis, with the exception of one day.

Subject Completion: A total of 6 subjects were entered into the study and all subjects completed one study.

Analytical Procedures

A. Quality Control

Standards and Controls: Calibration standards were prepared spiking a pool of human, interference-free, heparinized plasma with caffeine (USP Reference, Lot I). The plasma was obtained from Interstate Blood Bank (Memphis, Tenn.). The standards were prepared to contain 0.050, 0.100, 0.200, 0.500, 1.00, 2.00 and 5.00 µg/ml of caffeine.

The caffeine standards and controls were divided into 2.5 ml aliquots and stored in the laboratory in polypropylene snap-cap tubes frozen to at least −19° C.

The pre-study within-run coefficient of variation ranged from 0.915% to 2.54%. The relative accuracy of the procedure was estimated, through comparison of the measured concentration means of the control samples against their theoretical concentrations, and was found to average 99.5% for caffeine.

Run Acceptance Criteria: Chromatographic peak responses and peak response ratios were monitored using an electronic integrator. Each chromatographic tracing was inspected for acceptable retention times, peak shapes, resolution and integration before the peak response ratios (analyte-to-internal standard) were entered into the computer.

The acceptable limit of quantization for the run was evaluated through comparison of the mean response of the lowest concentration standards (0.050 µ/ml) with the responses of any interferences observed in the water blank, matrix blank and zero standard. The limit of quantization for the run was defined as the concentration at which the signal-to-noise ratio was at least 2.

Samples, standards and controls with an internal standard peak response which deviated more than ±25% from the mean within-run peak response of the internal standard (calculated for all standards and controls) were rejected.

The response ratio for each remaining non-zero standard was plotted as a function of concentration. A linear regression was calculated (R/S 1, version 4.3) by the method of least-squares using $(1/CONC)^2$ as a weighting factor. With this calibration line, a calculated concentration was determined for each standard sample. Any standard differing by more than ±25% from its theoretical value was excluded from the regression and the regression was recalculated. The analyte concentrations in the samples and the controls were estimated from the calibration line by use of the equation: (RATIO−INTERCEPT)/SLOPE.

The analytical run was considered acceptable if 4 of 6 controls passed established acceptance criteria and that at least one control sample was acceptable within each concentration range. Controls within an analytical run were considered acceptable if the low control values differed by no more than ±20% and the middle and high controls differed by no more than ±15% from their theoretical values. The concentrations o the controls were graphically displayed to permit visual confirmation of acceptability and identification of trends.

B. Sample Analysis

Sample Storage and Stability: The plasma samples, which were collected in the clinic were transferred to the laboratory and stored frozen to at least −19° C. until analyzed. Samples were not identified to the analysts by treatment group. All subjects' samples were analyzed within 19 days of the initial sampling. The frozen stability of caffeine in plasma has been confirmed for 138 days.

Peak Identification: The retention times of the analyte and the internal standard were identified, in any given analytical run, by comparison to stock standards chromatographed at the beginning of the run and to processed standards chromatographed through the run.

Pharmacokinetic and Statistical Procedures

A. Pharmacokinetic Data

All the available data from 6 subjects with reported caffeine concentrations were used in the pharmacokinetic analyses. Several subjects had pre-dose samples which contained measurable concentrations of caffeine. For each of these subject's data, the measured concentration at each sampling time was corrected by subtracting the level of caffeine at that time predicted from the decay of the pre-dose level. The decay curve was constructed using the elimination rate observed in the same period as the decay constant. After adjustment, each pre-dose level was 0.0 µg/ml, and each post-dose concentration was reduced accordingly.

Pharmacokinetic parameters (areas, times to peak, and elimination rates and half-lives) were calculated using the actual rather than the scheduled time of sample collection. Graphical presentations of individual subject results also used the exact times of sample collection. Graphical presentations of mean results used the scheduled times of sample collection.

Peak concentration (Cmax) was the observed maximum value (corrected for pre-dose levels, if necessary) during the collection period of 0 to 15 hours. The time to peak concentration (Tmax) was the time at which Cmax was observed (or first observed, if more than one peak was present).

The apparent first-order elimination rate (Ke) was estimated as the absolute value of the slope of the regression line for the terminal log-linear concentration-time values. The values included in the regression analyses were determined by examination of the individual subject plots of natural logarithm of concentration against time. Elimination half-life (t-½) was calculated as 0.693/Ke.

Area under the curve (AUC) to the time of the last non-zero concentration ($C_t$) was calculated by the linear trapezoidal method. Area to infinite time (AUCinf) was calculated by extrapolating AUC by the addition of the quantity: $C_t$/Ke.

B. Statistical Analyses

Statistical analyses were performed using the General Linear Models (GLM) procedures of the SAS statistical program. Hypothesis testing for treatment effects was conducted at $\alpha=0.05$. The statistical model contained main effects of sequence, subject within sequence, period, and treatment. Sequence effects were tested against the type III mean square term for subjects within sequence. All other main effects were tested against the mean square error term.

The observed and calculated pharmacokinetic parameters as well as the caffeine concentrations at each of the individual collection times were compared statistically.

Power for the pair-wise pharmacokinetic comparisons was calculated as the probability ($\alpha=0.05$) of detecting a difference equal to 20% of the mean for the reference treatment in the comparison, or a ratio of 1.25 for ln-transformed results. [Winer, B J. *Statistical Principles In Experimental Design*. NEW YORK: McGraw-Hill Book Company (1962) 21–26.]

Confidence Intervals (90%) for pair-wise area and peak concentrations comparisons were calculated by the t-test approach (2,1-sided) at $\alpha=0.05$ each side. The intervals were computed for the "true" mean test-to-reference treatment ratio (or geometric mean ratio for ln-transformed results).

Discussion and Results

Statistical analyses were performed on the caffeine data in order to compare the test chewing gum to the chewable reference tables. Natural log-transformation of the area and Cmax parameters was also performed and analyzed statistically. Table 1, which follows, summarizes the results (n=6) of the statistical analyses of the major bioavailability parameters.

Statistical comparisons of the test and reference formulations at each sampling time are summarized in Table 2.

Conclusion

The caffeine chewing gum pieces appear to have a much faster rate of absorption that the No-Doz® chewable tablets. The areas and peak concentrations of the chewing gum were less than half that of No-Doz® even though the gum base released one-half the caffeine that the tablet did. And the time to reach a peak for the gum was 30 minutes earlier than for the tablet.

TABLE 1

Comparisons of caffeine results for 50 mg chewing gum pieces (Test) vs. 100 mg No-Doz ® chewable tablets (Reference) administered as a single 100 mg dose under fasting conditions to 6 subjects.

| Parameter | Least Squares Means[1] | | Test/Ref. Ratio[2] | Power[3] | 90% Confidence Interval[4] | |
|---|---|---|---|---|---|---|
| | Test | Reference | | | Lower | Upper |
| AUC 0-t (µg-hr/ml) | 7.26 | 17.65 | 0.412* | 0.50 | 0.246 | 0.577 |
| AUCinf (µg-hr/ml) | 9.60 | 23.72 | 0.405* | 0.39 | 0.211 | 0.598 |
| Cmax (µg/ml) | 0.92 | 2.15 | 0.429* | 0.76 | 0.309 | 0.548 |
| Tmax (hour) | 1.08 | 1.58 | 0.684 | 0.22 | — | — |
| Ke (1/hour) | 0.1241 | 0.1058 | 1.173* | 0.86 | — | — |
| Elimhalf (hour) | 5.97 | 6.97 | 0.857* | 0.86 | — | — |
| Ln-Transformed Data | | | | | | |
| AUC 0-t (µg-hr/ml) | 6.22 | 17.44 | 0.357* | 0.15 | 0.239 | 0.532 |
| AUCinf (µg-hr/ml) | 7.66 | 23.00 | 0.333* | 0.13 | 0.212 | 0.524 |
| Cmax (µg/ml) | 0.84 | 2.14 | 0.391* | 0.17 | 0.272 | 0.562 |

[1]Least squares geometric means for ln-transformed data.
[2]Test/Ref Ratio calculated as Test mean divided by Reference mean.
[3]Power to detect a difference of 20% (original data) or a ratio of 1.25 (ln-transformed data).
[4]Confidence interval on the ratio.
*Detected as statistically significant by ANOVA ($\alpha = 0.05$).

TABLE 2

Summary of caffeine statistical comparisons at each sampling time comparing 50 mg chewing gum pieces (Test) vs. 100 mg No-Doz ® chewable tablets (Reference) administered as a single 100 mg dose under fasting conditions to 6 subjects.

| Sample Time | Collection (Hour) | Least Squares Means (µg/ml) | | Significance |
|---|---|---|---|---|
| | | Test | Reference | * |
| 1 | Pre-dose | 0.00 | 0.00 | — |
| 2 | 0.25 | 0.23 | 0.36 | 0.0269 |

TABLE 2-continued

Summary of caffeine statistical comparisons at each sampling time comparing 50 mg chewing gum pieces (Test) vs. 100 mg No-Doz ® chewable tablets (Reference) administered as a single 100 mg dose under fasting conditions to 6 subjects.

| Sample | Collection | Least Squares Means ($\mu$g/ml) | | Significance |
|---|---|---|---|---|
| Time | (Hour) | Test | Reference | * |
| 3 | 0.50 | 0.79 | 1.18 | None |
| 4 | 1.00 | 0.83 | 1.91 | 0.0008 |
| 5 | 1.50 | 0.84 | 2.05 | 0.0006 |
| 6 | 2.00 | 0.75 | 2.01 | 0.0004 |
| 7 | 2.50 | 0.72 | 1.92 | 0.0001 |
| 8 | 3.00 | 0.68 | 1.78 | 0.0006 |
| 9 | 4.00 | 0.66 | 1.64 | 0.0006 |
| 10 | 6.00 | 0.57 | 1.33 | 0.0046 |
| 11 | 8.00 | 0.47 | 1.10 | 0.0088 |
| 12 | 10.00 | 0.37 | 0.90 | 0.0052 |
| 13 | 12.00 | 0.28 | 0.75 | 0.0021 |
| 14 | 15.00 | 0.22 | 0.56 | 0.0068 |

*Statistical comparisons to test for the equivalence of treatment effects were performed at an a level of 0.05. The actual p-value is indicated at the time where statistically significant differences ($p < 0.05$) were detected; "None" indicates that no significance was detected ($p < 0.05$) at that time.

Figure 3:
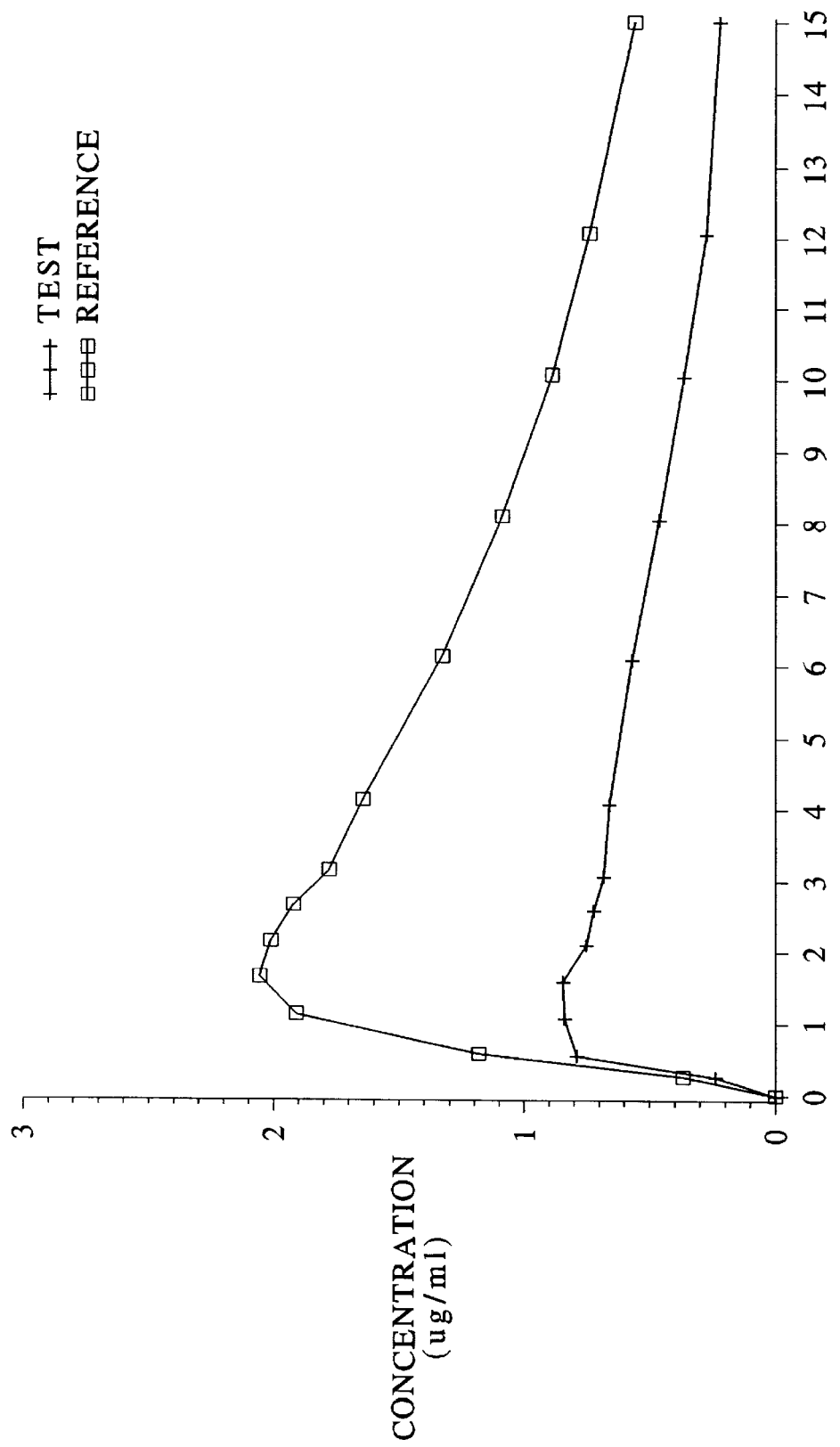
FIG. 3 illustrates graphically the results of Experiment No. 2 that is discussed supra.

FIG. 3 illustrates graphically least squares mean plasma concentration (~=6). Concentration of caffeine in (reg/ml) versus hours of the dose is illustrated graphically; chewing gum provided 50 mg of caffeine versus 100 mg of No-Doz® tablet. It should be noted that although in FIG. 2 the blood concentration level of caffeine is approximately 50% that of No-Doz®, the amount of caffeine delivered by the chewing gum was 50% that of the No-Doz®.

Experiment No. 3

The following protocol was followed. The chewing gum formula set forth on page 15 under the heading caffeine gum was used. Subjects chewed gum for 5 minutes. Then, the gum cuds were then collected and analyzed for caffeine. At T-10 minutes, the gum was collected after chewing for 10 minutes and then had the caffeine analyzed. This was repeated for all the time figures up to time 60 minutes. "Times 0" refers to non-chewed gum product. All these T-0 to T-60 minute gum samples were from the same lot of chewing gum.

The results are as follows:

TABLE 3

| Timed Chewed Minutes | Mg Caffeine remaining in gum | Actual % Caffeine remaining in gum | Relative % Caffeine remaining in gum |
|---|---|---|---|
| $T_0$ | 57.96 | 2.07 | 100.00 |
| $T_5$ | 16.80 | 0.60 | 28.70 |
| $T_{10}$ | 7.56 | 0.27 | 12.98 |
| $T_{20}$ | 1.68 | 0.06 | 3.01 |
| $T_{30}$ | 0.84 | 0.03 | 1.32 |
| $T_{40}$ | 0.00 | 0.00 | 0.00 |
| $T_{60}$ | 0.00 | 0.00 | 0.00 |

FIG. 3 illustrates graphically % caffeine remaining over chew-out time in minutes.

Experiment No. 4

To detect absorption in the oral cavity, the following experiment was carried out.

Samples of Stay-Alert Cinnamon flavored caffeine gum (Lot 713176) were analyzed for caffeine and found to contain 53.44±0.52 mg per stick. Two subject (S1 and S2) were recruited to chew the gum. Each subject chewed one stick of gum for 20 minutes, expectorating all saliva into a container. After chewing, each rinsed twice with 10 ml of water (20 ml total) and added the rinse water to the collected saliva. The volume of this solution was brought up to 75 ml with distilled water. S2 repeated the extraction process with a new stick of gum.

The chewed gum cuds and the saliva solutions were analyzed for caffeine by gas chromatography. (A spiking study was also conducted which showed recovery of caffeine from gum cuds and saliva solutions to be 99.25% and 103.50% respectively. Measured caffeine levels were not corrected for these recoveries as they were not deemed significantly different from 100%.) The results of the experiment are reported in Table 4.

TABLE 4

| | S1 | S2a | S2b |
|---|---|---|---|
| Volume of Saliva (ml) | 50 | 30 | 30 |
| Initial caffeine level (mg) | 53.44 | 53.44 | 53.44 |
| Caffeine remaining in cud (mg) | 2.00 | 13.09 | 15.12 |
| Caffeine in Saliva (mg) | 45.69 | 30.26 | 28.97 |
| Total Caffeine recovered (mg) | 47.69 | 43.35 | 44.09 |
| Unrecovered caffeine (mg) | 5.75 | 10.09 | 9.35 |
| Percent of released unrecovered | 11.2 | 25.0 | 24.4 |

It is believed that the unrecovered caffeine was adsorbed through mucous membranes in the oral cavity. Thus between 11 and 25% of the released caffeine was adsorbed orally. Note that the higher concentration of caffeine in saliva for S2 may have contributed to the higher adsorption in that subject.

Experiment No. 5
The following gum center formulation was made as a gum pellet center:

| Gum Center | % |
|---|---|
| Gum Base | 47.00 |
| Sorbitol | 39.52 |
| Liquid Sorbitol | 7.50 |
| Flavors | 2.36 |
| Encapsulated Flavors | 2.00 |
| Glycerin | 0.75 |
| Encapsulated Sweeteners | 0.87 |
| | 100.00 |

The gum pellet was coated with the following gum coating formulation:

| Gum Coating | % of Syrup 1 | % of Syrup 2 |
|---|---|---|
| Xylitol | 63.03 | 74.35 |
| Water | 11.14 | 13.15 |
| 40% Gum Tahla Solution | 20.87 | 7.96 |
| Titanium Dioxide Whitener | 0.37 | 0.44 |
| Peppermint Flavor[1] | 0.81 | 0.00 |
| Caffeine | 3.78 | 4.10 |
| | 100.00 | 100.00 |

[1]Flavor added in 2 additions after 10th and 15th within coating syrup 1.

Initial center piece weight was 0.956 grams. Gum was coated to a finished piece weight of 1.46 grams to give a 34.5% coating. Coating syrup 1 was used to coat the first 60% of the coating to a piece weight of 1.26 grams. Coating syrup 2 was used to coat to the final piece weight. Individual piece analysis of 5 pieces yielded a level of 26.1 mg of caffeine per piece. For a 2 piece dosage, caffeine level is 52.2 mg.

This gum product was used in a caffeine absorption study to compare release and absorption uptake of caffeine from gum and beverages. The test results showed that gum is a faster delivery vehicle for caffeine when compared to the same level in beverages as measured by blood plasma caffeine. Caffeine was taken up faster in the test subject's plasma after delivery via gum than after delivery of same caffeine dose via coffee, cola, and tea.

Comparisons of caffeine delivery between chewing gum and the three beverages are demonstrated by statistically significant differences in one or more of the following parameters:
1. Plasma caffeine concentration is significantly greater for gum vs. beverages within the first 10 to 30 minutes after caffeine delivery. This correlates to faster uptake.
2. Plasma absorption rate constant (A-rate) larger for gum vs. one or more beverages (2). Plasma absorption half life (abs. half-life) smaller for gum vs. one or more beverages (2). Time of peak caffeine plasma.

A clinical trial study was performed where six subjects participated in the test, blood was drawn and plasma separated. Blood sampling occurred prior to, and at present time intervals following a caffeine level of 50–55 mg released through the test delivery vehicle. Five different studies were completed: gum (with saliva swallowed, G2), gum (with saliva expectorated, G3), coffee (ingested COF), cola (ingested COK), and tea (ingested T). Blood samples of 5 ml were collected and the plasma portion separated, stored, and extracted and analyzed. A method was developed for the extraction and analysis of caffeine in fluids, which reports results as the concentration of caffeine in the plasma.

Data from the six subjects participating in the study were compiled, analyzed, and graphed, with mean plasma caffeine concentrations at specific time intervals determined. Analysis of variance (ANOVA) were performed on the means to determine statistical significance.

Pharmacokinetic parameters were determined through Wagner's 1967 Method of Residuals using a pharmacokinetic software package. Absorption rate constants and absorption half-life were also determined through the analysis of the absorption phase of the plots by linear regression since the absorption phase followed zero order kinetics.

The conclusions were as follows:
1. There was a faster uptake of caffeine in plasma during the early time intervals post dose 10 minutes to 25 minutes (T10–T25) via gum delivery vs. the same level of caffeine delivered via coffee and cola. For example, the average level of plasma caffeine (at T=10 minutes) present after gum chew is 0.545 $\mu$g/ml compared to 0.186 $\mu$g/ml for coffee and 0.236 $\mu$g/ml for cola. In other words, with the same level of caffeine being delivered from the three different vehicles, at T10 there is 3 times more caffeine present in plasma after chewing gum than from ingesting coffee and 2 times more caffeine from gum than from cola. The results of the tea study proved to be too variable due to instrument problems and repeat freeze/thawing of the samples. They were not included in the calculations.
2. Classical pharmacokinetic parameters, T-max, A-rate constant, abs. half-life, do not tell the story of faster uptake in the time interval of interest (T10–T25) in this study. This is due in part to the calculation using the Method of Residuals. This method was derived using classical pharmacokinetic curves which do not have much fluctuation in the data in that the drug concentration (usually measured every hour) increases to a sharp T-max, then decreases, without any fluctuation. In comparison, the data did contain minor fluctuations, due most likely to a combination of factors: measurement of plasma concentrations every five minutes rather than every quarter hour to one hours, caffeine binding with plasma protein, combination of both sublingual and gut absorption being detected. The plasma caffeine concentration followed the same trends as in classical pharmacokinetic curves, except that the concentration increased to a broad T-max, then decreased, and some of the points in the curve fluctuated up and down.

A-rate constant and abs. half-life determinations were also made through linear regression. No significant differences were noted in the means, though a trend was noted: the A-rate for the gum study (G2) was greater than that for coffee and cola for subjects 1–4 and the abs. half-life for the G2 study was less than that for coffee and cola for subjects 1–4. For example, the G2 abs. half-life averaged 13±4 minutes for subjects 1–4, 28±2 minutes for subjects 5 and 6, indicating faster absorption between the subjects. The amount of caffeine absorbed sublingually was 21±7 mg for subjects 1–4, and 10±1 mg for subjects 5 and 6 accounting for the increased A-rate and decreased abs. half-life in subjects 1–4. An ANOVA separating subjects 1–4 from 5 and 6 indicated that for subjects 1–4 cola abs. half-life is statistically greater than G2 abs. half-life (p=0.10), and the G2 A-rate is statistically greater than both the cola and coffee A-rate (p=0.05).
3. It was shown that significant levels of caffeine are absorbed sublingually directly into the bloodstream via delivery from gum. This was demonstrated through the testing of caffeinated gum where the saliva was expectorated. Even though the saliva was expectorated, 20–50% of the caffeine was absorbed through the oral cavity. This accounts for the early uptake into the bloodstream.

Experiment No. 6
The following formulation was made:

| Gum Center | % |
| --- | --- |
| Gum Base | 33.00 |
| Calcium Carbonate | 13.00 |
| Sorbitol | 44.23 |
| Glycerin | 4.00 |
| Flavors | 2.32 |
| Encapsulated Caffeine[2] | 1.50 |
| Free Caffeine | 0.45 |
| Lecithin | 0.60 |
| Encapsulated Sweeteners | 0.90 |
| | 100.00 |

[2]Spray dried maltodextrin/caffeine at 50% active caffeine.

| Gum Coating | Coating Syrup 3. % | Coating Syrup 4. % |
| --- | --- | --- |
| Xylitol | 64.14 | 76.23 |
| Water | 11.14 | 13.15 |
| 40% Gum Tahla Solution | 20.87 | 7.96 |
| Titanium Dioxide Whitener | 0.40 | 0.40 |
| Peppermint Flavor[3] | 1.40 | 0.00 |
| Sweeteners | 0.27 | 0.27 |

-continued

| Gum Coating | Coating Syrup 3. % | Coating Syrup 4. % |
|---|---|---|
| Carnauba Wax/ Talc Polishing Agents | 0.00 | 0.27[4] |
| Caffeine | 1.78 | 1.72 |
| | 100.00 | 100.00 |

[3]Flavor added in 3 additions after 3 separate syrup addition within coating syrup 1.
[4]Polished after completion of coating.

Initial center piece weight was 0.995 grams. Gum was coated to a finished piece weight of 1.52 grams to give a 34.5% coating. Coating syrup 3 was used to coat the first 60% of the coating to a piece weight of 1.30 grams. Coating syrup 4 was used to coat to the final piece weight. Individual piece analysis of 5 pieces yielded a level of 20.0±0.8 mg of caffeine per piece. For a two piece dosage, caffeine level is 40.0 mg.

This gum product was used in a caffeine absorption study to compare release and absorption uptake of caffeine from gum versus pills. The test results showed that gum is a faster delivery vehicle for caffeine when compared to a similar level in a pill as measured by blood plasma caffeine. Caffeine was taken up faster in the test subject's plasma after delivery via gum than after delivery of same caffeine dose via a pill.

Data from the six subjects participating in each study were compiled, analyzed, and graphed, with mean plasma caffeine concentrations at specific time intervals determined. Analysis of variance (ANOVA) and Student t-Tests were performed on the means to determine statistical significance. Pharmacokinetic parameters were done using a pharmacokinetic software package. The gums tested were pellet from Experiment No. 5, containing all the caffeine in the coating and delivering approximately 50 mg caffeine after chewing two pellets (designated as G2, G4, or 50 mg pellet), and Experiment No. 6, containing caffeine in the coating and center, and delivering approximately 40 mg caffeine after chewing two pellets (designated G5 or 40 mg pellet). Both pellets were compared to Pro-Plus™ 50 mg tablet is manufactured by the product license holder: PP Products, 40 Broadwater Road, Welayn Garden City, Harts, AL7 Bay, UK. Caffeine analysis were analyzed at 48.3 mg±1.4 mg caffeine per pill (avg. of n=5).

It was concluded that caffeine uptake in the bloodstream was faster for gum than a pill, based on the following:

1. Faster uptake of plasma caffeine via gum delivery was found during the early time intervals post dose 5 minutes to 50 minutes (T5–T50) when compared to the same level of caffeine delivered via a pill (50 mg). For example, with the same level of caffeine being delivered from the two different vehicles, on average, at T5 there is 30 times more caffeine detected in plasma after chewing gum (0.205 $\mu$g/ml). Average plasma caffeine levels significantly greater than the pill at a=0.01 for T5, and a=0.005 for T10.

2. Classical pharmacokinetic parameters, T-Max (time for peak plasma caffeine concentration) and Abs. half-life (absorbence half-life, time for caffeine concentration to be half of peak) were significantly different for caffeine delivered via 50 mg pellet gum (Experiment No. 5) than via a 50 mg pill. Faster uptake of plasma caffeine was demonstrated via delivery from gum compared to a pill due to the average plasma Abs. half-life and average plasma T-Max being significantly smaller for gum than the pill. For the 50 mg pellet gum, the average Abs. half-life=12.84 min. and the average T-Max=36.5 min. compared to the 50 mg pill with an average Abs. half-life=24.47 min (pill significantly greater than gum, a=0.0075), and an average T-Max=73.67 min (pill significantly greater than gum, a=0.0075), and an average T-Max=73.67 min (pill significantly greater than gum, a=0.005). In other words, after ingesting a pill, it takes a longer amount of time to reach half of the peak plasma caffeine concentration and the peak plasma caffeine concentration than after chewing gum delivering the same level of caffeine.

3. The Abs. Rate Const. (absorption rate constant, rate at which caffeine absorbs into the bloodstream) was significantly greater for 50 mg pellet gum (Experiment No. 5) than for the 50 mg pill, indicating that caffeine is absorbed at a greater rate after gum delivery than after delivery of the same dosage via a pill. For the 50 mg pellet gum, the average Abs. Rate Const.=0.060 compared to the 50 mg pill with an average Abs. Rate const.=0.031 (gum significantly greater than pill, a=0.005).

4. The test also demonstrated faster uptake of plasma caffeine via the product of Experiment No. 6, 40 mg pellet gum, delivery during the early time intervals post dose 10 minutes to 30 minutes (T10–T30) when compared to 50 mg of caffeine delivered via a pill. Significance levels ranged from a=0.05 to a=0.20. For example, the average level of plasma caffeine (at T=10 minutes) present after 40 mg pellet gum is chewed is 0.228 $\mu$g/ml compared to 0.034 ,g/ml for pill (difference was slightly significant, a=0.2). In other words, with caffeine being delivered from the two different vehicles at T10 there is 6.7 times more caffeine detected in plasma after chewing the product of Experiment No. 6 gum caffeine than after ingesting a pill, even though the pill delivered approximately 50 mg caffeine, and the product of Experiment No. 6 delivered approximately 40 mg. At T5, on average there was 13 times more caffeine detected in plasma after chewing Experiment No. 6 gum than after ingesting a pill.

5. Classical pharmacokinetic parameters, T-Max and Abs. half-life were significantly different for caffeine delivered via the product of Experiment No. 6 40 mg pellet gum than via a 50 mg pill. Faster uptake of plasma caffeine was demonstrated via delivery from the product of Experiment No. 6 gum compared to a pill due to the average plasma Abs. half-life and average plasma T-Max being significantly smaller for gum than the pill. For the 50 mg Experiment No. 5 gum, the average Abs. half-life=18.33 min. and the average T-Max=45 min compared to the 50 mg pill with an average Abs. half-life=24.47 min (pill significantly greater than gum, a=0.05), and an average T-Max=73.67 min (pill significantly greater than gum, a=0.15). Even though the product of Experiment No. 6 delivered 40 mg caffeine compared to delivery of 50 mg via a pill, it still took a longer amount of time to reach half of the peak plasma caffeine concentration for the pill than for the gum.

6. It was concluded that gums formulated with all the caffeine in the pellet coating delivered caffeine more quickly to the plasma than gums formulated with the caffeine split between the coating and the center based upon the following:

Classical pharmacokinetic parameters T-Max and Abs. half-life were greater than pill for both 50 mg pellet and Experiment No. 5 though the level of significant different was much greater for the 50 mg pellet (Experiment No. 5) (a=0.0075 and a=0.005 respectively) than the product of Experiment No. 6 (a=0.05, a=0.15). The Abs. Rate Const. was significantly lower for the pill than for either the 50 mg pellet or the the product of Experiment No. 6. Again, the level of significant difference was greater for the 50 mg pellet (experiment No. 5), a=0.005 compared to 0.20 for the product of Experiment No. 6.

7. Combining the conclusions from the two completed caffeine studies, it appears that rate of caffeine uptake in plasma via the various delivery vehicles tested follow this pattern:

Pellet with caffeine all in coating>Pellet with caffeine split between coating and center=Beverages coffee/cola>Pill Caffeine was chosen as a model for drug delivery tests because it is a food approved, pharmacologically active agent that is readily detected in plasma at a wide range of dosage levels. It is widely consumed via a number of delivery vehicles, including liquids (coffee, cola, and pills). Drugs are administered through different delivery vehicles, two oral delivery vehicles being liquid syrups and pills. Testing caffeinated beverages and pills vs. caffeinated gums should give an indication of how similar drugs administered as liquids or coated pills vs. coated gums could behave.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

We claim:

1. A chewing gum comprising:
    a tableted gum center comprising a water soluble portion and a water insoluble portion; and
    a coating comprising a medicament that surrounds the tableted gum center, the coating comprising at least 50% by weight of the chewing gum product.

2. The chewing gum of 1 wherein the medicament is selected from the group consisting of analgesics, muscle relaxants, antibiotics, antivirals, stimulants, antihistamines, decongestants, anti-inflammatories, antacids, psychotherapeutic agents, insulin, vitamins, minerals, and cardiovascular agents.

3. The chewing gum of claim 1 wherein the coating includes a sufficient amount of taste masking agent to provide acceptable organoleptic properties.

4. The chewing gum of claim 3 wherein the taste masking agent is selected from the group consisting of zinc gluconate, ethyl maltol, glycine, acesulfame-k, aspartame, saccharin, fructose, xylitol, isomalt, maltitol, spray dried licorice root, glycerrhizine, sodium gluconate, glucono delta-lactone, ethyl vanillin, dextrose, sucralose, vanillin, and ethyl maltol.

5. The chewing gum of claim 3 wherein the taste masking agent comprises approximately 30% to about 99% by weight of the coating.

6. The chewing gum of claim 1 wherein the coating includes approximately 0.5% to about 5% by weight of a high-intensity sweetener selected from the group consisting of aspartame, sucralose, saccharine, and acesulfame-k.

7. The chewing gum of claim 1 wherein the tableted gum center includes at least 50% by weight water-insoluble gum base.

8. The chewing gum of claim 1 wherein the coating does not have a shellac layer.

9. The chewing gum of claim 1 wherein the tableted gum center and coating are sugar-free.

10. A product including a medicament comprising:
    a tableted gum center comprising a water soluble portion and a water insoluble portion, the water insoluble portion comprising at least 30% by weight of the tableted gum center; and
    a coating that at least substantially surrounds the tableted gum center and comprises a medicament and a high-intensity sweetener, the coating comprising at least 50% by weight of the product.

11. The product of claim 10 wherein the medicament is selected from the group consisting of analgesics, muscle relaxants, antibiotics, antivirals, stimulants, antihistamines, decongestants, anti-inflammatories, antacids, psychotherapeutic agents, insulin, vitamins, minerals, and cardiovascular agents.

12. The product of claim 10 wherein the coating includes a sufficient amount of taste masking agent to provide acceptable organoleptic properties.

13. The product of claim 10 wherein the taste masking agent is selected from the group consisting of zinc gluconate, ethyl maltol, glycine, acesulfame-k, aspartame, saccharin, fructose, xylitol, isomalt, maltitol, spray dried licorice root, glycerrhizine, sodium gluconate, glucono delta-lactone, ethyl vanillin, dextrose, sucralose, vanillin, and ethyl maltol.

14. The product of claim 10 wherein the taste masking agent comprises approximately 30% to about 99% by weight of the coating.

15. The product of claim 10 wherein the coating includes approximately 0.5% to about 5% by weight of a high-intensity sweetener chosen from the group consisting of aspartame, sucralose, saccharine, and acesulfame-k.

16. The product of claim 10 wherein the coating comprises at least 70% by weight powder when it is applied to the tableted gum center.

17. The product of claim 10 wherein the product is sugar-free.

18. The chewing gum of claim 10 wherein the coating does not have a shellac layer.

19. A chewing gum product including a medicament comprising:
    a uniform gum center comprising a water-soluble and a water-insoluble portion; and
    a coating that substantially surrounds the uniform gum center and comprises a medicament, the coating comprising at least 50% by weight of the chewing gum product.

20. The chewing gum product of claim 19 wherein the medicament is selected from the group consisting of analgesics, muscle relaxants, antibiotics, antivirals, stimulants, antihistamines, decongestants, anti-inflammatories, antacids, psychotherapeutic agents, insulin, vitamins, minerals, and cardiovascular agents.

21. The chewing gum product of claim 19 wherein the coating includes a sufficient amount of taste masking agent to provide acceptable organoleptic properties.

22. The chewing gum product of claim 19 wherein the taste masking agent is selected from the group consisting of zinc gluconate, ethyl maltol, glycine, acesulfame-k, aspartame, saccharin, fructose, xylitol, isomalt, maltitol, spray dried licorice root, glycerrhizine, sodium gluconate, glucono delta-lactone, ethyl vanillin, dextrose, sucralose, vanillin, and ethyl maltol.

23. The chewing gum product of claim 19 wherein the taste masking agent comprises approximately 30% to about 99% by weight of the coating.

24. The chewing gum product of claim 19 wherein the coating includes approximately 0.5% to about 5% by weight of a high-intensity sweetener selected from the group consisting of aspartame, sucralose, saccharine, and acesulfame-k.

25. The chewing gum product of claim 19 wherein the tableted gum center includes at least 50% by weight water-insoluble gum base.

26. The chewing gum product of claim 19 wherein the coating does not have a shellac layer.

27. The chewing gum product of claim 19 wherein the tableted gum center and coating are sugar-free.

28. A product including a medicament comprising:

a gum center having a controlled size and shape and comprising a water-soluble and a water-insoluble portion; and a coating that substantially surrounds the gum center and comprises a medicament, the coating comprising at least 50% by weight of the product.

29. The product of claim 28 wherein the medicament is selected from the group consisting of analgesics, muscle relaxants, antibiotics, antivirals, stimulants, antihistamines, decongestants, anti-inflammatories, antacids, psychotherapeutic agents, insulin, vitamins, minerals, and cardiovascular agents.

30. The product of claim 28 wherein the coating includes a sufficient amount of taste masking agent to provide acceptable organoleptic properties.

31. The product of claim 28 wherein the taste masking agent is selected from the group consisting of zinc gluconate, ethyl maltol, glycine, acesulfame-k, aspartame, saccharin, fructose, xylitol, isomalt, maltitol, spray dried licorice root, glycerrhizine, sodium gluconate, glucono delta-lactone, ethyl vanillin, dextrose, sucralose, vanillin, and ethyl maltol.

32. The product of claim 28 wherein the taste masking agent comprises approximately 30% to about 99% by weight of the coating.

33. The product of claim 28 wherein the coating includes approximately 0.5% to about 5% by weight of a high-intensity sweetener selected from the group consisting of aspartame, sucralose, saccharine, and acesulfame-k.

34. The product of claim 28 wherein the tableted gum center includes at least 50% by weight water-insoluble gum base.

35. The product of claim 28 wherein the coating does not have a shellac layer.

36. The product of claim 28 wherein the tableted gum center and coating are sugar-free.

* * * * *